US00RE42315E

(19) United States
(12) Reissued Patent
Lopez et al.

(10) Patent Number: US RE42,315 E
(45) Date of Reissued Patent: May 3, 2011

(54) NANOSTRUCTURED SEPARATION AND ANALYSIS DEVICES FOR BIOLOGICAL MEMBRANES

(75) Inventors: Gabriel P. Lopez, Albuquerque, NM (US); Steven R. J. Brueck, Albuquerque, NM (US); Linnea K. Ista, Albuquerque, NM (US)

(73) Assignee: STC.UNM, Albuquerque, NM (US)

(21) Appl. No.: 11/825,298
(22) Filed: Jul. 5, 2007

Related U.S. Patent Documents

Reissue of:
(64) Patent No.: 6,913,697
Issued: Jul. 5, 2005
Appl. No.: 10/338,654
Filed: Jan. 9, 2003

U.S. Applications:
(63) Continuation-in-part of application No. 10/073,935, filed on Feb. 14, 2002, now Pat. No. 6,685,841
(60) Provisional application No. 60/347,002, filed on Jan. 11, 2002, and provisional application No. 60/268,365, filed on Feb. 14, 2001.

(51) Int. Cl.
*B01D 15/34* (2006.01)

(52) U.S. Cl. ..... 210/644; 210/198.2; 210/500.21; 210/511; 210/638; 210/645; 210/649; 210/650; 210/651; 210/656; 204/450; 422/101; 422/502; 422/527; 435/6; 435/7.1; 435/287.1; 435/287.2; 435/287.3; 436/177; 436/178; 530/412; 530/414; 977/702; 977/704; 977/705; 977/713; 977/714; 977/715; 977/920; 977/924

(58) Field of Classification Search ..... 210/500.21, 210/263, 321.84, 511, 634, 638, 644, 649–651, 210/198.2, 656, 660; 422/502, 503, 527, 422/534, 70, 100, 101; 436/161, 177, 178; 977/702–705, 713–717, 914, 920, 924, DIG. 1; 530/412–414; 435/4, 6, 7.1, 7.2, 287.1, 287.2, 435/287.3; 204/450, 451

See application file for complete search history.

(56) References Cited

U.S. PATENT DOCUMENTS 3,855,133 A 12/1974 Roehsler (Continued)

FOREIGN PATENT DOCUMENTS

DE 19712309 A1 5/1998

(Continued)

OTHER PUBLICATIONS

Volkmuth, et al. Observation of Electrophoresis of Single DNA Molecules in Nanofabricated Arrays. Presentation at joint annual meeting of Biophysical Society and the American Society for Biochemistry and Molecular Biology. Feb. 9–13, 1992.

Weigl, et al. Microfluidic Diffusion–Based Separation and Detection. Science. 1999; pp. 346–347.

Xu, et al. Dielectrophoresis of human red cells in microchips. Electrophoresis.1999;20:1829–1831.

(Continued)

*Primary Examiner*—Joseph W Drodge
(74) *Attorney, Agent, or Firm*—R. Neil Sudol; Henry D. Coleman; William J. Sapone

(57) ABSTRACT

The present invention provides a nanostructured device comprising a substrate including nanotroughs therein; and a lipid bilayer suspended on or supported in the substrate. A separation method is also provided comprising the steps of supporting or suspending a lipid bilayer on a substrate; wherein the substrate comprises nanostructures and wherein the lipid bilayer comprises at least one membrane associated biomolecule; and applying a driving force to the lipid bilayer to separate the membrane associated biomolecule from the lipid bilayer and to drive the membrane associated biomolecule into the nanostructures.

54 Claims, 9 Drawing Sheets

U.S. PATENT DOCUMENTS

| | | | | | |
|---|---|---|---|---|---|
| 3,906,929 | A | | 9/1975 | Augspurger | |
| 4,190,535 | A | | 2/1980 | Luderer et al. | |
| 4,801,380 | A | | 1/1989 | Parker et al. | |
| 4,814,082 | A | | 3/1989 | Wrasidlo | |
| 4,814,088 | A | | 3/1989 | Kutowy et al. | |
| 4,902,424 | A | | 2/1990 | Wrasidlo | |
| 4,906,439 | A | | 3/1990 | Grenner | |
| 4,915,839 | A | | 4/1990 | Marinaccio et al. | |
| 4,916,110 | A | | 4/1990 | Manniso | |
| 4,935,141 | A | | 6/1990 | Buck et al. | |
| 4,969,998 | A | | 11/1990 | Henn | |
| 4,971,904 | A | | 11/1990 | Luddy | |
| 4,977,078 | A | | 12/1990 | Niimura et al. | |
| 5,013,337 | A | | 5/1991 | Bedard et al. | |
| 5,019,263 | A | | 5/1991 | Haag et al. | |
| 5,130,025 | A | | 7/1992 | Lefebvre et al. | |
| 5,145,584 | A | | 9/1992 | Swamikannu | |
| 5,147,606 | A | | 9/1992 | Charlton et al. | |
| 5,204,239 | A | * | 4/1993 | Gitler et al. | 435/7.1 |
| 5,266,207 | A | | 11/1993 | Boye et al. | |
| 5,296,375 | A | | 3/1994 | Kricka et al. | |
| 5,304,487 | A | | 4/1994 | Wilding et al. | |
| 5,427,663 | A | | 6/1995 | Austin et al. | |
| 5,427,946 | A | | 6/1995 | Kricka et al. | |
| 5,474,675 | A | | 12/1995 | Kupka | |
| 5,541,072 | A | | 7/1996 | Wang et al. | |
| 5,587,070 | A | | 12/1996 | Pall et al. | |
| 5,622,831 | A | | 4/1997 | Liberti et al. | |
| 5,637,458 | A | | 6/1997 | Frankel et al. | |
| 5,639,669 | A | | 6/1997 | Ledley | |
| 5,674,592 | A | | 10/1997 | Clark et al. | |
| 5,707,799 | A | | 1/1998 | Hansmann et al. | |
| 5,709,943 | A | | 1/1998 | Coleman et al. | |
| 5,715,946 | A | | 2/1998 | Reichenbach | |
| 5,716,527 | A | | 2/1998 | Deckman et al. | |
| 5,750,339 | A | | 5/1998 | Smith | |
| 5,753,014 | A | | 5/1998 | Van Rijn | |
| 5,770,029 | A | | 6/1998 | Nelson et al. | |
| 5,798,042 | A | | 8/1998 | Chu et al. | |
| 5,837,115 | A | | 11/1998 | Austin et al. | |
| 5,843,767 | A | | 12/1998 | Beattie | |
| 5,858,188 | A | | 1/1999 | Soane et al. | |
| 5,858,195 | A | | 1/1999 | Ramsey | |
| 5,866,345 | A | | 2/1999 | Wilding et al. | |
| 5,871,650 | A | | 2/1999 | Lai et al. | |
| 5,876,830 | A | | 3/1999 | Michl et al. | |
| 5,891,651 | A | | 4/1999 | Roche et al. | |
| 5,928,880 | A | * | 7/1999 | Wilding et al. | 435/7.21 |
| 5,935,822 | A | * | 8/1999 | Staehelin et al. | 435/69.7 |
| 5,938,923 | A | | 8/1999 | Tu et al. | |
| 5,993,661 | A | | 11/1999 | Ruckenstein | |
| 6,007,690 | A | | 12/1999 | Nelson et al. | |
| 6,022,590 | A | | 2/2000 | Ferguson et al. | |
| 6,033,546 | A | | 3/2000 | Ramsey | |
| 6,043,177 | A | | 3/2000 | Falconer et al. | |
| 6,044,981 | A | | 4/2000 | Chu et al. | |
| 6,051,372 | A | | 4/2000 | Bayerl et al. | |
| 6,051,517 | A | | 4/2000 | Funke et al. | |
| 6,054,034 | A | | 4/2000 | Soane et al. | |
| 6,060,415 | A | | 5/2000 | Chao et al. | |
| 6,074,827 | A | | 6/2000 | Nelson et al. | |
| 6,090,289 | A | | 7/2000 | Verduijn et al. | |
| 6,100,393 | A | | 8/2000 | Lopez Ortiz et al. | |
| 6,113,794 | A | | 9/2000 | Kumar et al. | |
| 6,113,795 | A | | 9/2000 | Subramaniam et al. | |
| 6,132,607 | A | | 10/2000 | Chen et al. | |
| 6,143,576 | A | | 11/2000 | Buechler | |
| 6,156,270 | A | | 12/2000 | Buechler | |
| 6,177,373 | B1 | | 1/2001 | Sterte et al. | |
| 6,187,446 | B1 | | 2/2001 | Laurell et al. | |
| 6,190,638 | B1 | | 2/2001 | Anthonis et al. | |
| 6,197,523 | B1 | | 3/2001 | Rimm et al. | |
| 6,200,765 | B1 | | 3/2001 | Murphy et al. | |
| 6,241,894 | B1 | | 6/2001 | Briggs et al. | |
| 6,251,691 | B1 | | 6/2001 | Seul | |
| 6,261,928 | B1 | | 7/2001 | Bruel | |
| 6,264,044 | B1 | | 7/2001 | Meyering et al. | |
| 6,265,229 | B1 | | 7/2001 | Fodstad et al. | |
| 6,277,489 | B1 | | 8/2001 | Abbott et al. | |
| 6,306,659 | B1 | * | 10/2001 | Parce et al. | 436/47 |
| 6,309,798 | B1 | | 10/2001 | Reetz et al. | |
| 6,315,940 | B1 | | 11/2001 | Nisch et al. | |
| 6,344,326 | B1 | | 2/2002 | Nelson et al. | |
| 6,361,958 | B1 | | 3/2002 | Shieh et al. | |
| 6,368,871 | B1 | | 4/2002 | Christel et al. | |
| 6,377,057 | B1 | * | 4/2002 | Borkholder | 324/692 |
| 6,383,759 | B1 | | 5/2002 | Murphy et al. | |
| 6,387,290 | B1 | | 5/2002 | Brody et al. | |
| 6,432,630 | B1 | | 8/2002 | Blankenstein | |
| 6,444,461 | B1 | | 9/2002 | Knapp et al. | |
| 6,450,047 | B2 | * | 9/2002 | Swedberg et al. | 73/863 |
| 6,454,938 | B2 | | 9/2002 | Moon et al. | |
| 6,465,225 | B1 | | 10/2002 | Fuhr et al. | |
| 6,503,452 | B1 | * | 1/2003 | Boxer et al. | 506/23 |
| 6,540,895 | B1 | | 4/2003 | Spence et al. | |
| 6,570,196 | B1 | * | 5/2003 | Fromherz et al. | 257/213 |
| 6,576,478 | B1 | | 6/2003 | Wagner et al. | |
| 6,582,969 | B1 | | 6/2003 | Wagner et al. | |
| 6,596,144 | B1 | | 7/2003 | Regnier et al. | |
| 6,596,545 | B1 | * | 7/2003 | Wagner et al. | 506/7 |
| 6,613,525 | B2 | | 9/2003 | Nelson et al. | |
| 6,632,619 | B1 | | 10/2003 | Harrison et al. | |
| 6,635,163 | B1 | | 10/2003 | Han et al. | |
| 6,641,997 | B1 | * | 11/2003 | MacKinnon | 435/6 |
| 6,664,104 | B2 | | 12/2003 | Pourahmadi et al. | |
| 6,685,841 | B2 | | 2/2004 | Lopez et al. | |
| 6,699,719 | B2 | * | 3/2004 | Yamazaki et al. | 506/30 |
| 6,746,503 | B1 | | 6/2004 | Benett et al. | |
| 6,762,059 | B2 | | 7/2004 | Chan et al. | |
| 6,783,647 | B2 | | 8/2004 | Culbertson et al. | |
| 6,815,664 | B2 | | 11/2004 | Wang et al. | |
| 6,818,184 | B2 | | 11/2004 | Fulwyler et al. | |
| 6,878,271 | B2 | | 4/2005 | Gilbert et al. | |
| 6,881,315 | B2 | | 4/2005 | Iida et al. | |
| 6,893,881 | B1 | | 5/2005 | Fodstad et al. | |
| 6,911,345 | B2 | | 6/2005 | Quake et al. | |
| 6,913,697 | B2 | | 7/2005 | Lopez et al. | |
| 6,958,245 | B2 | | 10/2005 | Seul et al. | |
| 6,960,449 | B2 | | 11/2005 | Wang et al. | |
| 6,998,251 | B2 | * | 2/2006 | Guttman et al. | 435/41 |
| 7,150,812 | B2 | | 12/2006 | Huang et al. | |
| 2001/0036672 | A1 | | 11/2001 | Anderson et al. | |
| 2002/0005354 | A1 | | 1/2002 | Spence et al. | |
| 2002/0058332 | A1 | | 5/2002 | Quake et al. | |
| 2002/0090741 | A1 | | 7/2002 | Jurgensen et al. | |
| 2002/0108859 | A1 | | 8/2002 | Wang et al. | |
| 2002/0115163 | A1 | | 8/2002 | Wang et al. | |
| 2002/0115164 | A1 | | 8/2002 | Wang et al. | |
| 2002/0123078 | A1 | | 9/2002 | Seul et al. | |
| 2002/0123112 | A1 | | 9/2002 | Wang et al. | |
| 2002/0132315 | A1 | | 9/2002 | Wang et al. | |
| 2002/0132316 | A1 | | 9/2002 | Wang et al. | |
| 2002/0172987 | A1 | | 11/2002 | Terstappen et al. | |
| 2003/0072682 | A1 | | 4/2003 | Kikinis | |
| 2003/0077292 | A1 | | 4/2003 | Hanash et al. | |
| 2003/0159999 | A1 | | 8/2003 | Oakey et al. | |
| 2004/0018116 | A1 | | 1/2004 | Desmond et al. | |
| 2004/0072278 | A1 | | 4/2004 | Chou et al. | |
| 2004/0121343 | A1 | | 6/2004 | Buechler et al. | |
| 2004/0144651 | A1 | | 7/2004 | Huang et al. | |
| 2004/0232074 | A1 | | 11/2004 | Peters et al. | |

| | | | |
|---|---|---|---|
| 2004/0245102 | A1 | 12/2004 | Gilbert et al. |
| 2005/0049793 | A1 | 3/2005 | Paterlini-Brechot |
| 2005/0092662 | A1 | 5/2005 | Gilbert et al. |
| 2005/0123454 | A1 | 6/2005 | Cox |
| 2005/0142663 | A1 | 6/2005 | Parthasarathy et al. |
| 2005/0145497 | A1 | 7/2005 | Gilbert et al. |
| 2005/0164158 | A1 | 7/2005 | Wang et al. |
| 2005/0170373 | A1 | 8/2005 | Monforte |
| 2005/0170418 | A1 | 8/2005 | Moreland et al. |
| 2005/0175996 | A1 | 8/2005 | Chen |
| 2005/0191636 | A1 | 9/2005 | Hahn |
| 2005/0211556 | A1 | 9/2005 | Childers et al. |
| 2005/0236314 | A1 | 10/2005 | Neyer et al. |
| 2005/0239101 | A1 | 10/2005 | Sukumar et al. |
| 2005/0244843 | A1 | 11/2005 | Chen et al. |
| 2005/0250111 | A1 | 11/2005 | Xie et al. |
| 2005/0250199 | A1 | 11/2005 | Anderson et al. |
| 2005/0252840 | A1 | 11/2005 | Arnold et al. |
| 2005/0262577 | A1 | 11/2005 | Guelly et al. |
| 2005/0266433 | A1 | 12/2005 | Kapur et al. |
| 2005/0282196 | A1 | 12/2005 | Costa |
| 2006/0051265 | A1 | 3/2006 | Mohamed et al. |
| 2006/0060767 | A1 | 3/2006 | Wang et al. |
| 2006/0134599 | A1 | 6/2006 | Toner et al. |
| 2006/0160243 | A1 | 7/2006 | Tang et al. |
| 2006/0223178 | A1 | 10/2006 | Barber et al. |
| 2006/0252054 | A1 | 11/2006 | Lin et al. |
| 2006/0252087 | A1 | 11/2006 | Tang et al. |
| 2007/0026381 | A1 | 2/2007 | Huang et al. |
| 2007/0026413 | A1 | 2/2007 | Fuchs et al. |
| 2007/0026414 | A1 | 2/2007 | Fuchs et al. |
| 2007/0026415 | A1 | 2/2007 | Fuchs et al. |
| 2007/0026416 | A1 | 2/2007 | Fuchs |
| 2007/0026417 | A1 | 2/2007 | Fuchs et al. |
| 2007/0026418 | A1 | 2/2007 | Fuchs et al. |
| 2007/0026419 | A1 | 2/2007 | Fuchs et al. |
| 2007/0026469 | A1 | 2/2007 | Fuchs et al. |
| 2007/0059680 | A1 | 3/2007 | Kapur et al. |
| 2007/0059683 | A1 | 3/2007 | Barber et al. |
| 2007/0059716 | A1 | 3/2007 | Balis et al. |
| 2007/0059718 | A1 | 3/2007 | Toner et al. |
| 2007/0059719 | A1 | 3/2007 | Grisham et al. |
| 2007/0059774 | A1 | 3/2007 | Grisham et al. |
| 2007/0059781 | A1 | 3/2007 | Kapur et al. |
| 2007/0099207 | A1 | 5/2007 | Fuchs et al. |

FOREIGN PATENT DOCUMENTS

| | | | |
|---|---|---|---|
| EP | 0057907 | | 8/1982 |
| EP | 0094193 | | 11/1983 |
| EP | 1221342 | A2 | 7/2002 |
| EP | 1338894 | A2 | 8/2003 |
| EP | 1418003 | A1 | 5/2004 |
| EP | 1462800 | A1 | 9/2004 |
| EP | 0919812 | B1 | 10/2004 |
| WO | WO 93/22053 | A1 | 11/1993 |
| WO | WO 94/29707 | A1 | 12/1994 |
| WO | WO 98/10267 | A1 | 3/1998 |
| WO | WO 99/44064 | A1 | 9/1999 |
| WO | WO 00/62931 | A1 | 10/2000 |
| WO | WO 02/12896 | A1 | 2/2002 |
| WO | WO 02/28523 | A2 | 4/2002 |
| WO | WO 02/30562 | A1 | 4/2002 |
| WO | WO 03/000418 | A2 | 1/2003 |
| WO | WO 03/031938 | A2 | 4/2003 |
| WO | WO 03/035894 | A2 | 5/2003 |
| WO | WO 03/079006 | A1 | 9/2003 |
| WO | WO 03/085379 | A2 | 10/2003 |
| WO | WO 2004/004906 | A1 | 1/2004 |
| WO | WO 2004/015411 | A1 | 2/2004 |
| WO | WO 2004/024327 | A1 | 3/2004 |
| WO | WO 2004/029221 | A2 | 4/2004 |
| WO | WO 2004/037374 | A2 | 5/2004 |
| WO | WO 2004/056978 | A1 | 7/2004 |
| WO | WO 2004/113877 | A1 | 12/2004 |
| WO | WO 2005/043121 | A2 | 5/2005 |
| WO | WO 2005/047529 | A1 | 5/2005 |
| WO | WO 2005/049168 | A2 | 6/2005 |
| WO | WO 2005/058937 | A2 | 6/2005 |
| WO | WO 2005/068503 | A2 | 7/2005 |
| WO | WO 2005/084374 | A2 | 9/2005 |
| WO | WO 2005/085861 | A2 | 9/2005 |
| WO | WO 2005/108621 | A1 | 11/2005 |
| WO | WO 2005/109238 | A2 | 11/2005 |
| WO | WO 2005/121362 | A2 | 12/2005 |
| WO | WO 2006/078470 | A2 | 7/2006 |

OTHER PUBLICATIONS

Zaidi, et al. Optical properties of nanoscale, one–dimensional silicon grating structures. Journal of Applied Physics. 1996; 80(12):6997–7008.

Zankovych, et al. Nanoimprint lithography: challenges and prospects. Nanotechnology. 2001; 12(2): 91–5.

Zhang, et al. High–speed free–flow electrophoresis on chip. Anal Chem. 2003;75:5759–5766.

Zuska, P. Microtechnology Opens Doors to the Universe of Small Space, MD&DI Jan. 1997, p. 131.

Kapur, et al, U.S. Appl. No. 11/227,904, entitled "Devices And Methods For Enrichment And Alteration Of Cells And Other Particles," filed Sep. 15, 2005.

"Micromechanics Imitate Blood Vessels" Design News 15 (Mar. 22, 1993).

Archer, et al. Cell Reactions to Dielectrophoretic Manipulation. Biochemical and Biophysical Research Communications. 1999;257:687–98.

Ashcroft, et al. Solid State Physics. Saunders College Publishing. Orlando, FL. 1976. (Table of Contents only.).

Babochkina, T. I. Ph. D. Dissertation—Fetal cells in maternal circulating: Fetal cell separation and FISH analysis. University of Basel, Switzerland. Dec. 8, 2005. (123 pages).

Bauer, J. Advances in cell separation: recent developments in counterflow centrifugal elutriation and continuous flow cell separation. Journal of Chromatography. 1999;722:55–69.

Becker, et al. Fabrication of Microstructures With High Aspect Ratios and Great Structural Heights by Synchrotron Radiation Lithography, Galvanoforming, and Plastic Moulding (LIGA Process). Microelectronic Engineering. 1986;4:35–56.

Becker, et al. Planar quartz chips with submicron channels for two–dimensional capillary electrophoresis applications. J. Micromech Microeng.1998;9:24–28.

Beebe et al. Functional Hydrogel Structures for Autonomous Flow Control Inside Microfluidic Channels. Nature. 2000; 404:588–590.

Benincasa, et al. Cell Sorting by One Gravity SPLITT Fractionation. Analytical Chemistry. 2005; 77(16):5294–5301.

Berg, H. C. Random Walks in Biology, Ch. 4. Princeton University Press. Princeton, NJ. 1993. pp. 48–64.

Cao, et al. Fabrication of 10 nm enclosed nanofluidic channels. Applied Physics Letters. 2002; 81(1): 174–6.

Cao, et al. Gradient nanostructures for interfacing microfluidics and nanofluidics. Applied Physics Letters. 2002; 81(16): 3058–60.

Carlson, et al. Self–Sorting of White Blood Cells in a Lattice. Phys. Rev. Lett. 79:2149–2152 (1997).

Chiu, et al. Patterned Deposition of Cells and Proteins Onto Surfaces by Using Three–Dimensional Microfluidic Systems. Proceedings of the National Academy of Sciences of the United States of America. 2000; pp. 2408–2413.
Chou, et al. A Microfabricated Device for Sizing and Sorting DNA Molecules. Proceedings of the National Academy of Sciences of the United States of America. 1999; pp. 11–13.
Chou, et al. Imprint of sub–25 nm vias and trenches in polymers. Applied Physics Letters. 1995; 67(21): 3114–6.
Chou, et al. Sorting by diffusion: An asymmetric obstacle course for continuous molecular separation. PNAS. 1999; 96(24):13762–13765.
Colburn, et al. Patterning nonflat substrates with a low pressure, room temperature, imprint lithography process. Journal of Vacuum Science & Technology B (Microelectronics and Nanometer Structures). 2001; 19(6):2162–72.
Craighead, et al. Nanoelectromechanical systems. Science. 2000; 290(5496): 1532–5.
Das, et al. Dielectrophoretic segregation of different human cell types on microscope slides. Anal. Chem. 2005; 77:2708–2719.
De Kretser, et al. The Separation of Cell Populations using Monoclonal Antibodies attached to Sepharose. Tissue Antigens. 1980;16:317–325.
Delamarche, et al. Microfluidic Networks for Chemical Patterning of Substrates: Design and Application to Bioassays. Journal of the American Chemical Society. 1998; 120:500–508.
Delamarche, et al. Patterned Delivery of Immunoglobulins to Surfaces Using Microfluidic Networks. Science. 1997; 276:779–781.
Deshmukh, et al. Continuous Micromixer With Pulsatile Micropumps. Solid–State Sensor and Actuator Workshop. Hilton Head Island, South Carolina; Jun. 4–8, 2000:73–76.
Doyle, et al. Self–Assembled Magnetic Matrices for DNA Separation Chips. Science 295:2237 (2002).
Eigen, et al. Sorting Single Molecules: Application to Diagnostics and Evolutionary Biotechnology. Proceedings of the National Academy of Sciences of the United States of America. 1994; 91:5740–5747.
Evans, et al. The Bubble Spring and Channel (BSAC) Valve: An Actuated, Bi–Stable Mechanical Valve For In–Plane Fluid Control. Transducers '99. Sendai, Japan; Jun. 7–10, 1999.
Fan, et al. Molecular dynamics simulation of a liquid in a complex nano channel flow. Physics of Fluids. 2002; 14(3): 1146–53.
Farooqui, et al. Microfabrication of Submicron Nozzles in Silicon Nitride. Journal of Microelectromechanical Systems. 1992; 1(2):86–88.
Fiedler, et al. Dielectrophoretic Sorting of Particles and Cells in a Microsystem. Analytical Chemistry. 1998; pp. 1909–1915.
Freemantle, M. Downsizing Chemistry. Chemical analysis and synthesis on microchips promise a variety of potential benefits. Chemical & Engineering News. 1999; pp. 27–36.
Fu, et al. An integrated microfabricated cell sorter. Anal Chem. 2002;74:2451–2457.
Fu, et al. A Microfabricated Flourescence–Activated Cell Sorter. Nature Biotechnology.1999; 17:1109–1111.
Fuhr, et al. Biological Application of Microstructures. Topics in Current Chemistry. 1997; 194:83–116.
Giddings, J.C. Unified Separation Science. John Wiley & Sons, Inc. 1991; Cover Page & Table of Contents only.
Giddings, J. C. Chemistry 'Eddy' Diffusion in Chromatography. Nature. 1959;184:357–358.
Giddings, J. C. Field–Flow Fractionation: Analysis of Macromolecular, Colloidal, and Particulate Materials. Science. 1993;260:1456–1465.
Han, et al. Separation of Long DNA Molecules in a Microfabricated Entropic Trap Array. Science. 2000;288:1026–1029.
Harnett, et al. Heat–depolymerizable polycarbonates as electron beam patternable sacrifical layers for nanofluidics. Journal of Vacuum Science & Technology B (Microelectronics and Nanometer Structures). 2001; 19(6): 2842–5.
Hibara, et al. Nanochannels on a fused–silica microchip and liquid properties investigation by time–resolved fluorescence measurements. Analytical Chemistry. 2002; 74(24): 6170–6.
Huang, et al. A DNA prism for high–speed continuous fractionation of large DNA molecules. Nature Biotechnology. 2002;20:1048–1051.
Huang, et al. Continuous Particle Separation Through Deterministic Lateral Displacement Science 304:987–90 (2004).
Huang, et al. Electric Manipulation of Bioparticles and Macromoledules on Microfabricated Electrodes. Analytical Chemistry. 2001; pp. 1549–1559.
Huang, et al. Role of Molecular Size in Ratchet Fractionation. 2002; 89(17):178301–1–178301–4.
Huh, et al. Gravity–driven microhydrodynamics–based cell sorter (microHYCS) for rapid, inexpensive, and efficient cell separation and size–profiling. 2nd Annual International IEEE–EMBS Special Topic Conference on Microtechnology in Medicine and Biology. Madison, Wisconsin USA; May 2–4, 2002:466–469.
Ivker, M. Direct Observation of Reptation in Artificial Gel Environments. Bachelor of Arts thesis, Princeton University. Spring 1991.
Jeon, et al. Generation of Solution and surface Gradients Using Microfluidic Systems. Langmuir. 2000, pp. 8311–8316.
Kamholz, et al. Quantitative Analysis of Molecular Interaction in a Microfluidic Channel: the T–Sensor. Analytical Chemistry. 1999; pp. 5340–5347.
Kenis, et al. Microfabrication Inside Capillaries Using Multiphase Laminar Flow Patterning. Science. 1999; 285:83–85.
Kim, et al. Polymer microstructures formed by moulding in capillaries. Nature. 1995;376:581–584.
Kumar, et al. Cell Separation: A Review. Pathology. 1984;16:53–62.
Li, et al. Transport, Manipulation, and Reaction of Biological Cells On–Chip Using Electrokinetic Effects. Analytical Chemistry., 1997; pp. 1564–1568.
Mehrishi , et al. Electrophoresis of cells and the biological relevance of surface charge. Electrophoresis.2002;23:1984–1994.
Mohamed, et al. Development of a rare cell fractionation device: application for cancer detection. IEEE Trans Nanobioscience. 2004; 3(4): 251–6.
Moore, et al. Lymphocyte fractionation using immunomagnetic colloid and a dipole magnet flow cell sorter. J Biochem Biophys Methods. 1998;37:11–33.
Oakey et al. Laminar Flow–Based Separations at the Microscale. Biotechnology Progress. 2002; pp. 1439–1442.

Olson, et al. An In Situ Flow Cytometer for the Optical Analysis of Individual Particles in Seawater. Available at http://www.whoi.edu/science/B/Olsonlab/insitu2001.htm. Accessed Apr. 24, 2006.
Petersen, et al. The Promise of Miniaturized Clinical Diagnostic Systems. IVD Technol. 4:43–49 (1998).
Product literature for GEM, a system for blood testing: GEM Premier 3000. Avaiable at http://www.ilus.com/premier_gem3000_iqm.asp. Accessed Apr. 24, 2006.
Raymond, et al. Continuous Separation of High Molecular Weight Compounds Using a Microliter Volume Free–Flow Electrophoresis Microstructure. 1996;68:2515–2522.
Rice, et al. Electrokinetic flow in a cylindrical capillary. Journal of Physical Chemistry. 1965; 69(11): 4017–24.
Sethu, et al. Continuous Flow Microfluidic Device for Rapid Erythrocyte Lysis. Anal. Chem. 76:6247–6253 (2004).
Studer, et al. Nanoembossing of thermoplastic polymers for microfluidic applications. Applied Physics Letters. 2002; 80(19): 3614–6.
Takayama, et al. Patterning Cells and Their Environments Using Multiple Laminar Fluid Flows in Capillary Networks. Proceedings of the National Academy of Sciences of the United States of America. 1999:5545–5548.
Takayama, et al. Subcellular Position of Small Molecues. Nature. 2001; 411:1016.
Toner, et al. Blood–on–a–Chip. Annu. Rev. Biomed. Eng. 7:77–103, C1–C3 (2005).
Tong, et al. Low Temperature Wafer Direct Bonding. Journal of Microelectromechanical Systems. 1994;3:29–35.
Turner, et al. Confinement–Induced Entropic Recoil of Single DNA Molecules in a Nanofluidic Structure. Physical Review Letters.2002;88:128103.1–128103.4.
Voldman, et al. Holding Forces of Single–Particle Dielectrophoretic Traps. Biophysical Journal.2001;80:531–541.
Volkmuth, et al. DNA electrophoresis in microlithographic arrays. Nature. 1992; 358:600–602.

* cited by examiner

NANOSTRUCTURED SEPARATION AND ANALYSIS DEVICES FOR BIOLOGICAL MEMBRANES

Matter enclosed in heavy brackets [ ] appears in the original patent but forms no part of this reissue specification; matter printed in italics indicates the additions made by reissue.

CROSS-REFERENCE TO RELATED APPLICATIONS

*This is an application for reissue of U.S. Pat. No. 6,913,697. More than one reissue application has been filed for the reissue of U.S. Pat. No. 6,913,697. The reissue applications include the present application and co-pending U.S. patent application Ser. Nos. 12/215,893, 12/217,113, and 12/217,114 all of which are Divisional Reissue Applications, filed as divisionals of the present application, filed as a Reissue of U.S. Pat. No. 6,913,697 issued on Jul. 5, 2005, which was filed as application Ser. No. 10/338,654 entitled "Nanostructured Separation and Analysis Devices for Biological Membranes," on Jan. 9, 2003, as a Continuation-in-Part of U.S. patent application Ser. No. 10/073,935, entitled "Nanostructured Devices for Separation and Analysis," filed on Feb. 14, 2002, now U.S. Pat. No. 6,685,841 issued on Feb. 3, 2004, which claims priority to U.S. Provisional patent application Ser. No. 60/268,365, entitled "Nanostructured Devices for Separation and Analysis," filed on Feb. 14, 2001. This application also claims priority to U.S. Provisional patent application Ser. No. 60/347,002, entitled "Nanostructured Devices," filed on Jan. 11, 2002. The entire contents and disclosures of the above applications are hereby incorporated by reference.*

GOVERNMENT INTEREST STATEMENT

This invention is made with government support under grant number DAAD19-99-1-0196 awarded by the United States Army Research Office. The government has certain rights in this invention.

BACKGROUND OF THE INVENTION

1. Field of the Invention

The present invention relates to the fabrication of nanostructured matrices for use in supporting lipid bilayers for the separation and analysis of membrane-associated molecules.

2. Description of the Prior Art

The demand for precise separation of molecules using small sample volumes is increasing. Currently, polyacrylamide gel electrophoresis (PAGE) remains the standard for protein separation and identification in biotechnology. However, the set of separation strategies that rely on this technique are hampered by: (1) inconvenience of preparation of the variety of gels needed for the separations, (2) inherent inconsistencies in production conditions; and therefore, irreproducibility between different batches of gels, (3) susceptibility of the polymer to degradation under high electric fields, (4) lack of reusability, (5) difficulty in incorporation of these techniques into strategies for development of multidimensional (multi-technique) integrated separation systems, and (6) limited resolution and dynamic range of biomolecular separations.

Gradient PAGE techniques utilize one-dimensional filtration by manipulating pore-size though control of crosslinker, monomer, and solvent concentrations. Such separation matrices are recognized as having the potential to maintain excellent resolution and dynamic range. However, their utility is greatly hampered by the need for cumbersome gel preparation protocols and lack of reproducibility.

In general, the separation of molecules across matrices or membranes has been known in the art. Such separations are typically achieved by employing barriers that allow cut-offs at a precise molecular weight or by size-exclusion. The art describes structures where molecular transport and filtration take place perpendicular to the surface of the separating material. These currently available systems, however, suffer from a number of drawbacks: (1) the matrices formed are generally composed of non-uniform structures, (2) even where a gradation in size of structures is required, they may be random or at best have to be serially and sequentially arrayed through a cumbersome process of lithography, (3) fabrications of separation devices pose problems in terms of batch-to-batch variations; and consequently, poor reproducibility of results therefrom, (4) lack of efficiency of separation, (5) loss of sample volume, and (6) biomolecules may not be amenable to separation by many of the available systems.

Thus far, the most relevant work has been the development of "Brownian ratchets" in which assymetric diffusion leads to separation of molecules based on their size (van Oudenaarden et al., Science, 285: 1046-1052, 1999, the entire contents and disclosure of which is hereby incorporated by reference). Subsequently, Chou et al. (see, Chou et al., Proc. Natl. Acad. Sci., 96, 13762-13765, 1999, the entire contents and disclosure of which is hereby incorporated by reference) attempted separation of DNA molecules using Microsystems formed by conventional photolithography. Although such prior work demonstrated that relatively simple 3-dimensional architectures could lead to effective separation, the developments have not gained ground with the biotechnological community. The primary reasons for this lack of acceptance being the difficulty of preparation of the nanofluidic systems and the associated high-cost of fabrication.

Similarly, "artificial gels" incorporating regular arrays of nanoscale pillars created through electron beam and/or imprint lithography have been described, for instance, in U.S. Pat. No. 6,110,339 to Yager, et al. and by Turner, et al. (J. Vac. Sci. Technol. B., 16 3835-3840, 1998, the entire contents and disclosure of which is hereby incorporated by reference). Such nanolithographically-defined structures utilize regular arrays of uniform-sized nanostructures throughout the separation matrix. Although these nanolithographic structures are useful in separation, the systems suffer from drawbacks: (1) resolution limitations, (2) flexibility limitations, and (3) difficulty in integrating the system with other, more complex, separation devices. Thus, the need for an efficient, highly-resolving, flexible, cost-efficient, and reproducible molecular-separation matrix, is largely unmet. The analysis and characterization of biomolecules is further limited by the difficulty in separating membrane-associated molecules. Typically, detergents are used to remove transmembrane molecules, but even mild detergents may denature such molecules, rendering them inactive and/or disrupting necessary functional interactions with other membrane components including other proteins or lipid components. Additionally, the study of biomolecules is limited by the difficulty in fabricating a cellular environment that allows for the interaction of molecules. Such interactions may be useful in studying molecular transport and communication across cell membranes.

Thus far, the most relevant work in this area is the use of synthetic lipid bilayer membranes as separation platforms for biomolecules. Because of their planar structure, such membranes are more amenable to laboratory use. The separation technology is achieved by integrating planar lipid bilayers with varied surfaces to allow for separation of molecules. For instance, synthetic membranes supported on a glass or silica surface allow for the electrophoretic separation of labeled phospholipids and membrane proteins. See, Groves, J. T. and Boxer, S. G., Electric-field-induced concentration gradients in planar supported bilayers, Biophysical Journal, 69: 1972-1975 (1995), and Groves, J. T., Wulfing, C., and Boxer, S. G., Electrical manipulation of glycan phosphatidyl inositol tethered proteins in planar supported bilayers, Biophysical Journal, 71: 2716-2723 (1996), the entire contents and disclosures of which are hereby incorporated by reference. Additionally, lipid bilayer membranes have been incorporated into microstructured devices by lithographically-derived features to partition the supported membrane into separate regions to pattern the distribution of the lipid bilayer over the surface or as a coating for microchannels. See, Cremer, P. S., and Yang, T., Creating spatially addressed arrays of planar supported fluid phospholipid membranes, Proceedings of the National Academy of Sciences, U.S.A., 121: 8130-8131; Nissen, J., Jacobs, K., and Radler, J. O., Interface dynamics of lipid membrane spreading on solid surfaces, Physical Review Letters, 86: 1904-1907 (2001); and Yang, T. L., Jung, S. Y., Mao, H. B., and Cremer, P. S., Fabrication of phospholipid bilayer-coated microchannels for on-chip immunoassays, Analytical Chemistry, 73: 165-169 (2001), the entire contents and disclosures of which are hereby incorporated by reference. Furthermore, lipid bilayers have been supported on nanostructured arrays to produce Brownian ratchets utilized in the electrophoresis of fluorescent phospholipids. See, van Oudenaarden, A., and Boxer, S. G., Brownian ratchets: Molecular separations in lipid bilayers supported on patterned arrays, Science, 285: 1046-1048 (1999), the entire contents and disclosures of which are hereby incorporated by reference. Finally, hybrid lipid bilayers, in which one leaflet (define leaflet) of the supported membrane is formed by an alkane-thiol monolayer on gold, have shown promise for use in bioseparations. See, Plant, A., Supported hybrid bilayer membranes as rugged cell membrane mimics, Langmuir, 15: 5128-5135 (1999), and Hui, et al., U.S. Pat. No. 5,919,576, the entire contents and disclosures of which are hereby incorporated by reference. However, in these techniques, the close proximity or constraint of the lower leaflet to the supporting surface reduces their usefulness in analyzing transmembrane proteins or interactions between cytoplasmic and extracellular components of the membrane.

Also relevant to the technology of the present invention are previous methods for creating suspended lipid bilayers in which regions of the lipid bilayers are freely suspended between two aqueous reservoirs. Such hybrid bilayers are formed so one leaflet of the suspended region of the bilayer is replaced with a methyl terminated self-assembled monolayer, allowing for suspension of free bilayers over gaps as large as 100 μm. See, Ogier, S. D., Bushby, R. J., Cheng, Y., Evans, S. D., Evand, S. W., Jenkins, T. A., Knowles, P. F., and Miles, R. E., Langmuir, 16: 5696-5701 (2000), the entire contents and disclosures of which are hereby incorporated by reference. Although these types of suspended bilayers have been used for studying membrane permeability and transmembrane protein function, the use of such suspended lipid bilayers in the separation of transmembrane proteins has not been examined. Thus, the need for technology that utilizes supported and suspended lipid bilayer membranes that allow for (1) separation of membrane-spanning complexes, and (2) cellular interaction is largely unmet.

SUMMARY OF THE INVENTION

It is therefore an object of the present invention to provide an efficient nanostructured matrix for separation and analysis of molecules.

It is a further object of the present invention to provide a matrix that enables gradient or non-uniform transport of molecules across a plane parallel to the surface of the matrix.

A further object of the present invention is to enable integration of multi-dimensional multi-technique molecular separation systems into a single platform.

Yet another object of the present invention is to provide for customized fabrication of a nanostructured separation matrix including an array having a gradient property.

It is yet another object of the present invention is to provide a nanostructured matrix that may cater to different ranges of molecular separations, in terms of resolution and dynamics.

Another object of the present invention is to enable consistency in the composition of the nanostructures forming the separation matrix.

Yet another object of the present invention is to enable separation and/or identification of a molecular species.

A further object of the present invention is to enable calibration-free use of the separation/analysis process.

Yet another object of the present invention is to enable multiple use of a single separation matrix.

A further object of the present invention is to enable parallel production of separation matrices at relatively low cost.

In all of the above embodiments, it is an object to provide enhanced reproducibility and resolution in the separation of molecules.

According to a first broad aspect of the present invention, there is provided a nanostructured device comprising a substrate including at least one nanotrough therein; and a lipid bilayer suspended on the substrate.

According to second broad aspect of the invention, there is provided a nanostructured device comprising a substrate including at least one nanotrough therein; and at least one lipid bilayer supported in at least one of the at least one nanotroughs.

According to a third broad aspect of the invention, there is provided a separation method comprising the steps of supporting or suspending a lipid bilayer on a substrate; wherein the substrate comprises at least one nanostructure and wherein the lipid bilayer comprises at least one membrane associated biomolecule; and applying a driving force to the lipid bilayer to separate the at least one membrane associated biomolecule from the lipid bilayer and to drive the at least one membrane associated biomolecule into the at least one nanostructure.

Other objects and features of the present invention will be apparent from the following detailed description of the preferred embodiment.

BRIEF DESCRIPTION OF THE DRAWINGS

The invention will be described in conjunction with the accompanying drawings, in which.

DETAILED DESCRIPTION OF THE PREFERRED EMBODIMENT

Figure 1:
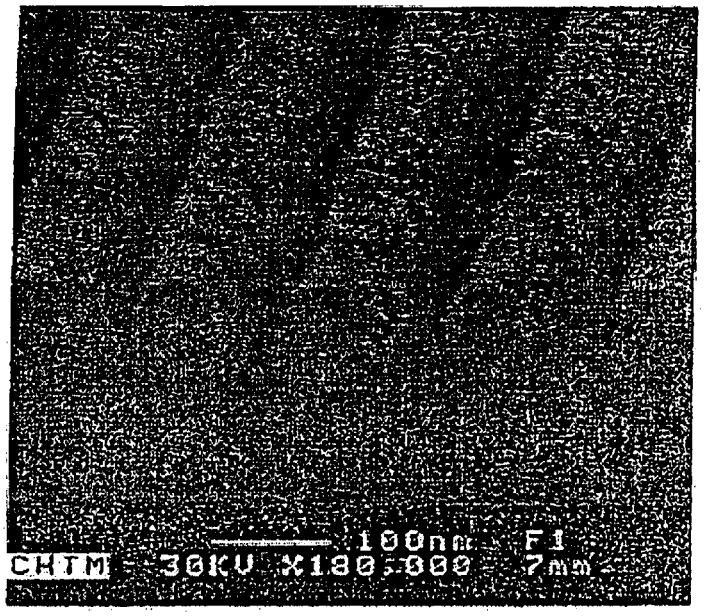
FIG. 1 is a micrograph showing a 150-nm period photoresist grating written with 213 nm light.

It is advantageous to define several terms before describing the invention. It should be appreciated that the following definitions are used throughout this application.

Definitions

Where the definition of terms departs from the commonly used meaning of the term, applicant intends to utilize the definitions provided below, unless specifically indicated.

For the purposes of the present invention, the term "nanostructure" refers to a protrusion or void having a diameter in at least one direction of 1 to 500 nm.

For the purposes of the present invention, the term "diameter" refers to the distance across a nanostructure through the middle and perpendicular to the axis of the nanostructure, parallel to the plane of the substrate (upon which the nanostructure is located).

For the purposes of the present invention, the tern "axis" refers to a line running along the middle of a nanostructure in the direction the nanostructure's longest dimension parallel to the surface of the substrate on which the nanostructure is located.

For the purposes of the present invention, the term "protrusion" refers to a structure that protrudes from the surface of a substrate or that protrudes from a portion of a substrate that has been etched. The protrusions of the present invention may be any convenient size or shape. The cross-section of a protrusion may be circular, square, rectangular, oval, elliptical, etc.

For the purposes of the present invention, the term "channel" refers to a gap between any two protrusions. The channels of the present invention may be any convenient size or shape.

For the purposes of the present invention, the term "array" refers to an arrangement of nanostructures.

For the purposes of the present invention, the term "gradient" refers to an array where channels, protrusions or other features at one end of the array are larger than those at an opposite end of the array.

For the purposes of the present invention, the term "continuous gradient" refers to a gradient where successive rows of channels, protrusions or other features decrease in size substantially continuously from one end of the gradient to the other end of the gradient.

For the purposes of the present invention, the term "non-continuous gradient" refers to a gradient that includes regions of the gradient having successive rows of channels, protrusions or other features that are substantially the same size.

For the purposes of the present invention, the term "matrix" refers to a substrate having an array of nanostructures present on or in at least a portion of the substrate. A matrix of the present invention preferably has at least one gradient on or in the substrate formed by the nanostructures. Examples of a matrix of the present invention include one or more arrays located on a chip, such as a semiconductor chip, biochip, etc. Methods for making biochips which may be readily adapted for use in making biochips of the present invention are described in U.S. Pat. No. 6,174,683, the entire contents and disclosure of which is hereby incorporated by reference.

For the purposes of the present invention, the term "interferometric lithography" (IL) refers to a process of lithography that involves interference patterns of two (or more) mutually coherent light waves. The angles between the light propagation vectors of the waves are sufficiently large to produce an interference pattern that has a high spatial frequency. The resulting interference pattern may have nanoscale dimensions. Examples of interferometric lithography techniques that may be used in the present invention are described in Chen X L, Brueck S R J, "Imaging interferometric lithography: approaching the limits of optics" in *Optics Letters,* 24, pp. 124-126 (1999), in "Imaging interferometric lithography: A wavelength division multiplex approach to extending optical lithography, Chen X L, Brueck S R J,*Journal of Vacuum Science and Technology B,* vol. 16, pp. 3392-3397 (1998), in U.S. Pat. No. 5,759,744 to Brueck et al., in U.S. Pat. No. 6,233,044 to Brueck et al., and U.S. Pat. No. 6,042,998 to Brueck et al., the entire contents and disclosures of which are hereby incorporated by reference.

For the purposes of the present invention, the term "biomolecules" refers to biologically derived molecules such as peptides, small polypeptides, long polypeptides, proteins, antigens, antibodies, tagged proteins, oligonucleotides, nucleotides, polynucleotides, aptamers, DNA, RNA, carbohydrates, etc., and complexes thereof.

For the purposes of the present invention, the term "size exclusion separation process" refers to separating particles, such as biomolecules, by size based on the ability of smaller particles to pass through smaller openings or channels than larger particles.

For the purposes of the present invention, the term "gel electrophoretic mobility separation process" refers to any conventional electrophoresis separation technique such as two-dimensional polyacrylamide gel electrophoresis. Polyacrylamide gel electrophoresis (PAGE) is used to separate biomolecules, usually proteins or DNA fragments, by the ratio of each biomolecule's mass to charge. Proteins may be separated in either their native state, or denatured by the addition of a detergent such as SDS (Sodium Dodecyl Sulfate). Further resolution may be obtained in some cases by making a gel with a gradient either in the concentration of the acrylamide or in the degree of crosslinking within the gel matrix. An array of the present invention may be used in performing equivalent molecular weight separations, with either electrical currents or flow as the driving force.

For the purposes of the present invention, the term "isoelectric focusing separation process" refers to the separation of charged biomolecules, such as proteins and peptides, by each biomolecule's isoelectric point. A pH gradient is generally generated using a mixture of ampholytes within the separation matrix, usually polycrylamide. The biomolecules in the mixture then migrate to the region where the pH is equal to a particular biomolecule's isoelectric point, at which time the charged biomolecule becomes electrically neutral. This technique, combined with subsequent separation by SDS-PAGE, is used in traditional two-dimensional gel electrophoresis. Similar pH gradients may be generated using an array of the present invention including a two-dimensional gradient, using traditional isolectric focusing with soluble ampholytes or by using chemical patterning techniques, or immobilization of ampholytes after electrical focusing. Examples of capillary-based isoelectric focusing separation processes suitable for use with the present invention are described in Thorman, Tsai, Michaud, Mosher and Bier, Capillary Isoelectric-Focusing: Effects of Capillary, Geometry, Voltage Gradient and Addition of Linear Polymer, J. Chromatography, 398:75-86 (1987), the entire contents and disclosure of which are hereby incorporated by reference.

For the purposes of the present invention, the term "asymmetric diffusion separation process" refers to a separation process in which steric constraints drive diffusion preferentially in one direction. Examples of asymmetric diffusion separation processes suitable for use with the present invention are described in Van Oudenaarden et al., Science, 285: 1046-1052 (1999), the entire contents and disclosure of which are hereby incorporated by reference.

For the purposes of the present invention, the term "entropic trapping separation process" refers to separations using nanostructured devices of alternating thin and thick regions, with the thin regions being smaller than the radius of gyration of the biomolecule being separated. Under an electrical field, the molecules repeatedly change conformation, costing entropic free energy, thus limiting mobility. An example of an entropic trapping separation process suitable for use with the present invention is described in Han J, Craighead H D, Separation of long DNA molecules in a microfabricated entropic trap array, Science, 288:1026-1029 (2000), the entire contents and disclosure of which is hereby incorporated by reference.

For the purposes of the present invention, the term "hydrophobic interaction chromatography separation process" refers to a technique whereby molecules are partitioned between a hydrophobic matrix and a hydrophilic solvent. The degree of hydrophobicity of the target molecule determines the target molecule's retention time. The array of the present invention may be modified to incorporate a gradient of hydrophobicities or to create a milieu in which the hydrophobicity may be rapidly and reversibly changed, thus providing a driving force for molecular movement.

For the purposes of the present invention, the term "affinity chromatography separation process" refers to a chromatography process that takes advantage of specific chemical interactions between a target molecule and a chromatographic matrix. One of the most widely used forms of affinity chromatography employs immunoaffinity in which an antibody or series of antibodies are immobilized on a support. Other affinity agents include enzymes that interact with specific targets or receptors. Another example of affinity chromatography is a molecular recognition separation process such as the separation of long DNA molecules in a microfabricated entropic trap array. An array of the present invention may be used for both the generation of affinity matrices and for the subsequent use of affinity matrices.

For the purposes of the present invention, the term "enantiomeric resolution separation process" refers to a process to separate organic particles, such as biomolecules by chirality. Enantiomeric resolution is especially important in carbohydrate separations where differences between different glycosides are exclusively enantiomeric. Indeed, common chiral selectors are cyclodextrins used in capillary electrophoresis. Macrocyclic antibiotics and crown ethers are commonly used selectors. Selectors may be used either globally or in zones of an array of the present invention to confer yet another means of separation.

For the purposes of the present invention, the term "capillary electrophoresis separation process" refers to a separation process in which separation takes place in a liquid rather than in a gel matrix. Capillary electrophoresis allows for separations to be done on smaller quantities of material and with improved resolution in comparison to conventional gel electrophoresis processes. The channels in an array of the present invention may be arranged to generate a capillary type arrangement in a second direction following separations based on chemical properties (e.g., IEF, affinity, hydrophobic interaction chromatography or enantiomeric separation) or capillaries may be applied as a third dimension.

For the purposes of the present invention, the phrase "comprises Si" refers to silicon and any silicon complex, compound, etc. that includes silicon, such as $SiO_2$, glass, etc.

For the purposes of the present invention, the term "lipid" refers to conventional lipids, phospholipids, etc.

For the purposes of the present invention, the term "lipid bilayer" refers to any double layer of oriented amphipathic lipid molecules in which the hydrocarbon tails face inward to form a continous nonpolar phase.

For the purposes of the present invention, the term "simple bilayer" refers to a conventional lipid bilayer in which the bilayer is formed from micelles of phospholipids with or without membrane proteins.

For the purposes of the present invention, the term "hybrid bilayer" refers to a bilayer that is derived from more than one source, either through mixing of micelles before formation, or post bilayer fusion. These also refer to bilayers in which one component is synthetically derived, or in which one leaflet is supported on the nanotextured surface prior to bilayer formation.

For the purposes of the present invention, the term "self-assembled monolayer hybrid bilayer" refers to a hybrid bilayer in which the synthetic portion is composed of a self-assembled monolayer of silanes or ω-substituted alkanethilates on gold.

Figure 9:
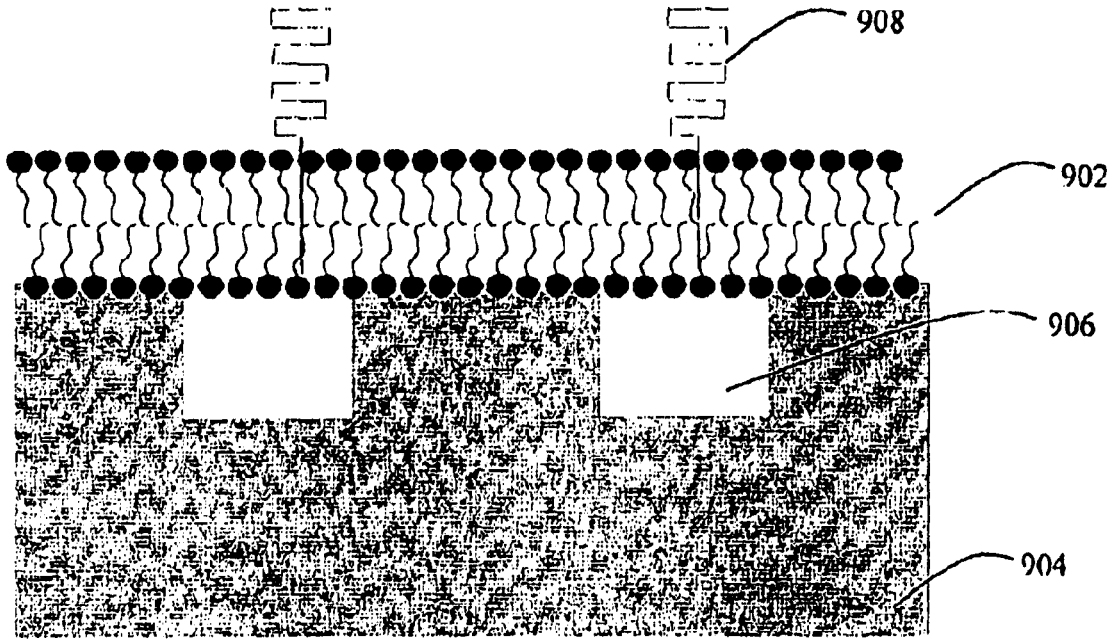
FIG. 9 shows a lipid bilayer suspended on a nanostructure according to an embodiment of the present invention.
Figure 10:
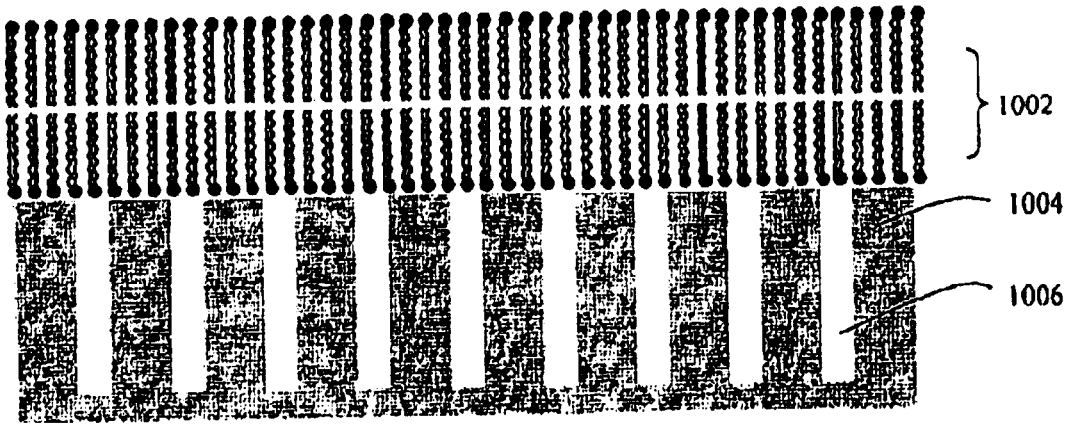
FIG. 10 shows a suspended bilayer on a nanostructure according to an embodiment of the present invention.
Figure 11:
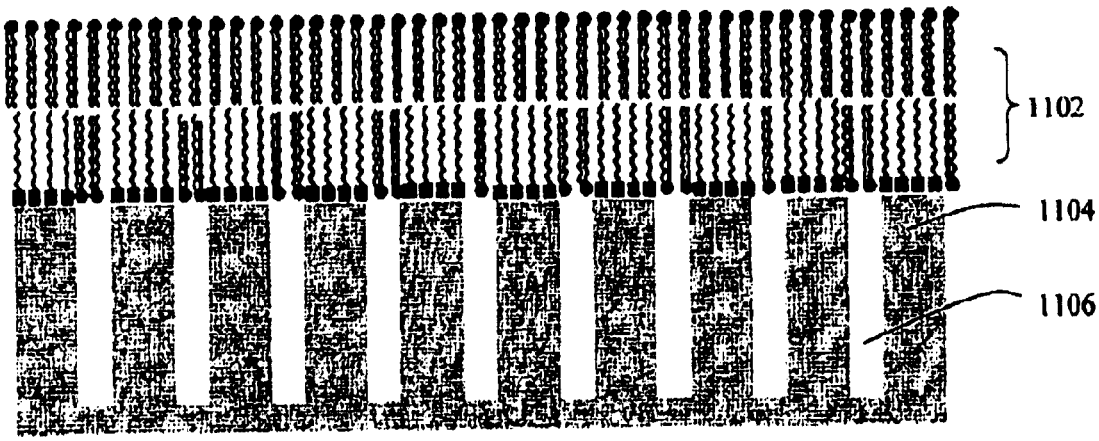
FIG. 11 shows a suspended lipid/self-assembled monolayer hybrid bilayer on a nanostructure according to an embodiment of the present invention.

For the purposes of the present invention, the term "suspended" refers to bilayers present on a nanostructure and located above nanotroughs in a nanostructure. An example of a suspended bilayer is shown in FIGS. 9, 10 and 11.

Figure 12:
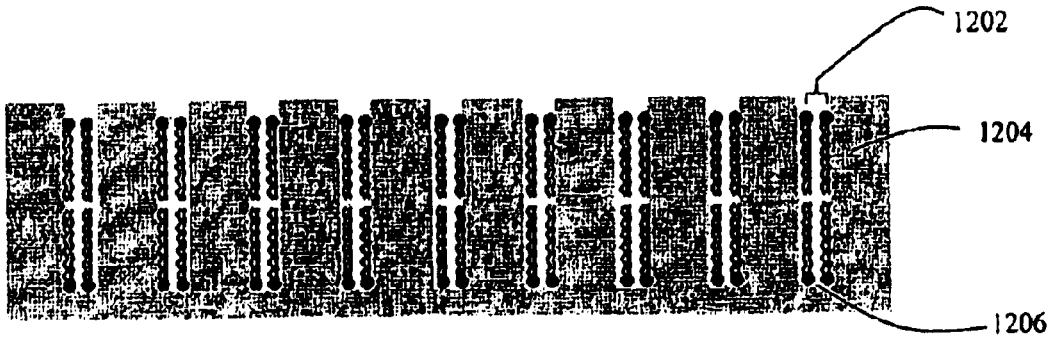
FIG. 12 shows a bilayer supported in nanotroughs of a nanostructure according to an embodiment of the present invention.

For the purposes of the present invention, the term "supported" refers to bilayers located in nanotroughs of a nanostructure. An example of a supported bilayer is shown in FIG. 12.

For the purposes of the present invention, the term "nanotrough" refers to a trough with a void dimension of 1-500 nm, whether uniform or not.

For the purposes of the present invention, the term "leaflet" refers to one half of a fluid bilayer membrane composed of a single layer of phospholipids and any included proteins.

For the purposes of the present invention, the term "filled with at least one fluid" refers to a nanostructure, preferably a nanotrough or channel, containing a fluid that is at least partially contained within said nanostructure. The nanostructure does not need to be completely filled with a fluid according to this definition.

For the purposes of the present invention, the term "membrane associated biomolecule" refers to any membrane associated biomolecule, such as transmembrane proteins, membrane phospholipids, lipophilic biomolecules, complexes thereof, etc.

Description

The present invention provides, in part, for robust, inexpensive and reproducible methods for forming separation matrices for gradient separations based on, for example, electrophoresis and size exclusion that includes all the positive traits of gradient PAGE. These matrices may be adapted for a host of variant separation strategies, including electrophoresis, detergent solubilization, native electrophoresis, isoelectric focusing, 2D-electrophoresis, hydrophobic interaction, and affinity chromatography. More specifically, the present invention provides for the use of such separation matrices as support for lipid bilayers that serve as separation platforms for membrane-associated biomolecules. The methods of fabrication discussed herein may also be adapted to existing microfabrication and integration facilities.

The present invention provides for separation of molecular species across a nanostructured matrix, a method of fabricating nanostructures comprising the matrix and the use of such a matrix for separation and/or analysis of molecules by defining the physical size and/or chemical features of the nanostructures as a means of screening. The nanostructured matrix may be used to separate biological materials, such as proteins, carbohydrates, and nucleic acids as well as nonbiological materials, such as synthetic polymers. These nanostructures may be made out of a variety of materials, including silicon, thus providing systems that may be easily chemically modified for additional flexibility. The use of lithography to generate nanostructured separation matrices has advantages over other techniques (such as traditional acrylamide gel polymerization) since it (1) creates highly ordered structures, (2) gives the possibility of creating macroscopic arrays of continually varying size or chemistry across one dimension, (3) is highly reproducible, and (4) may be easily implemented in the creation of complex, integrated separation systems that are disposable or reusable. Furthermore, the use of lithographically defined separation matrices lends itself to the facile implementation of these matrices into multi-level, 3-dimensional separation devices in which different screening mechanisms allow enhanced separations. Particularly, the lithographic nanostructured surfaces may be used to support lipid bilayers or hybrid lipid bilayers for separating membrane-associated molecules and studying cellular interactions. The present invention aims to (1) eliminate some of the current limitations by the fabrication of highly uniform and reproducible nanostructured separation systems prepared by nano-and microlithography, and (2) eliminate some of the current limitations by utilizing the lithographic nanostructured surfaces in conjunction with lipid bilayers to produce separation platforms for membrane-associated molecules. Nanolithographically-Defined Gradients:

Using an advanced lithographic technique such as interferometric lithography (IL) capable of producing nanostructures, patterns of nanostructures may be rapidly created over wide, macroscopic areas at low cost (compared to other techniques such as electron beam lithography). In addition, it may be used to easily generate arrays of nanostructures (protrusions or channels) whose dimensions vary semi-continuously in the plane of surface of the material being patterned. IL has advantages over other methods that might be used to construct nanopatterned fluidic structures (e.g., electron beam lithography, X-ray lithography, or local probe lithography) due to the low cost of implementation and the parallel nature of the lithographic technique. Combining IL with conventional lithography allows for the formation of device structures in individual areas and the addition of aperiodic features such as electronic and fluidic connections. Imaging interferometric lithography extends optics to fundamental, deep-subwavelength scales.

Figure 2:
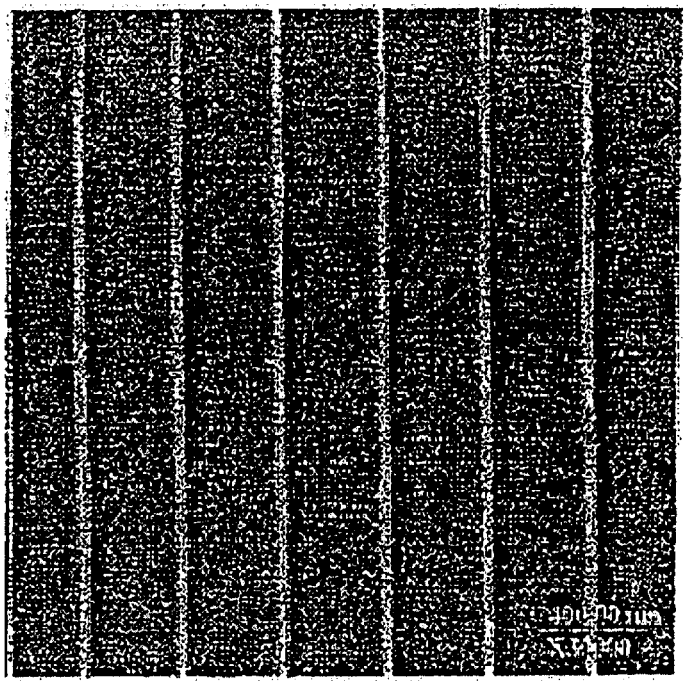
FIG. 2 is a micrograph showing 30-nm photoresist lines.

It is worthwhile at this point to consider the fundamental limits of optical lithography. For the interference of two plane waves in air, the period is given by $\lambda/(2 \sin \theta)$ where $\lambda$ is the optical wavelength and $\theta$ is the angle of incidence. For a 213-nm laser source (fifth harmonic of YAG) this gives a period of ~150 nm (for $\theta$=80°). FIG. 1 shows an example of a large-area, 150 nm period, photoresist grating. It is important to realize that this limit is on the period, not on the feature dimensions. Nonlinearities in the exposure/develop processes and in subsequent processing may reduce the feature to dimensions well below $\lambda/4$. An example in FIG. 2 shows 30-nm developed resist lines on a 360-nm pitch written at a wavelength of 364 nm. The ultimate limit in linewidth is set by material properties and by uniformity of the processing; linewidths as small as 10 nm are routinely achieved. The use of immersion techniques may further reduce the period by a factor of the refractive index, approximately a factor of 1.5, to a period of ~75 nm. Initial results reproduced the 150 nm pitch of FIG. 1 at a lower angle of incidence.

Figure 3:
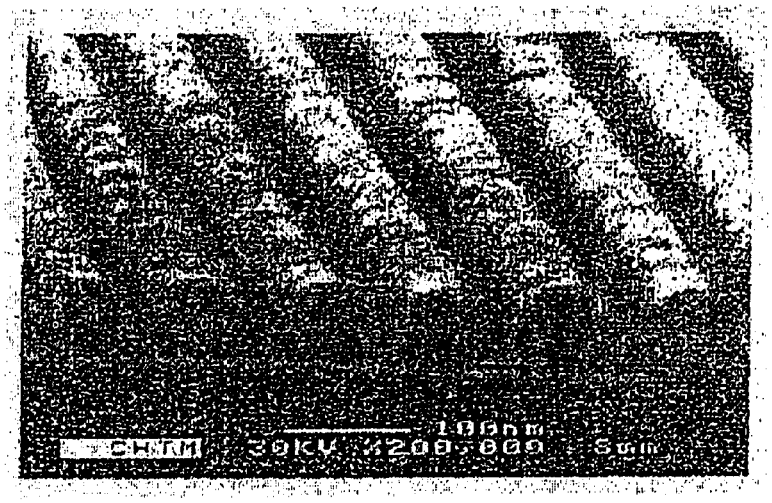
FIG. 3 is a micrograph showing a 108-nm pitch photoresist grating, written using 213 nm light, and immersion in DI water.

Water and higher-index liquids, including liquid Ar (n~1.6), may be used to further extend these results into the sub-100-nm period regime that will be important for biological separations. FIG. 3 shows an initial example of immersion interferometric lithography where the grating period has been reduced to 108 nm with exposure by 213 nm light using immersion in deionized water.

Figure 4:
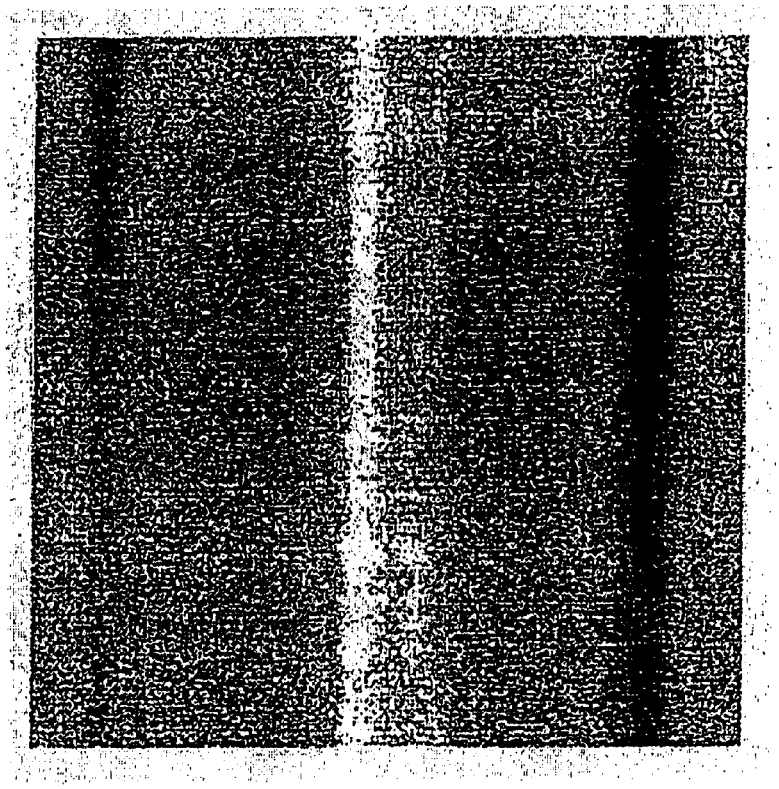
FIG. 4 is a micrograph showing a photoresist line interpolated between two lines etched 360 nm apart into a nitride film demonstrating spatial period division to exent the spatial frequency coverage of optical lithography.
Figures 5A, 5B:
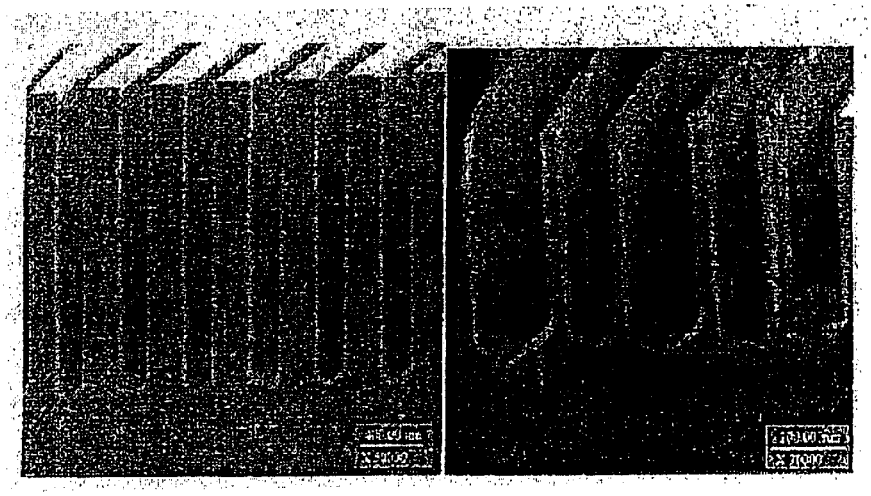
FIGS. 5A and 5B are micrographs showing transfer of interferometric lithography patterns into deep structures in Si using KOH anisotropic etching, with FIG. 5A showing the original period of 360 m with about 1 micrometer deep etched grooves and FIG. 5B showing the 180 nm period, frequency-doubled structure corresponding to the lithographic result of FIG. 4.

Nonlinear processes may be used to further reduce the period. FIG. 4 shows an example of a photoresist line interpolated between two parallel lines that have already been transferred into a nitride layer. FIG. 5B shows the result of transferring both of these patterns into Si using a KOH etch process. The final period is ~half of the initial IL period. Extending the calculation above with this spatial period division gives a period of ~37 nm and a dense linewidth of ~17 nm ($\lambda/12$).

Importantly, all of these results are macroscopic in scale, e.g., covering areas of ~1 $cm^2$ or larger. A strength of optics is the parallel nature of the exposure, which may be cm's or larger in extent. For a square lattice with a 100-nm pitch and a 1 cm field, there are $10^{10}$ features, well beyond the realistic capabilities of serial techniques such as e-beam and scanning probes. In particular embodiments of the present invention, IL may be extended deep into the nanometer regime (either to feature sizes of ~10 nm or nearest-neighbor distances (aperture sizes) of <10 nm, but not both simultaneously).

A continuously varying channel spacing between nanostructures is desired for many of the bio-separation applications such as various nanofluidic configurations discussed herein.

One approach to a graded structure is to macroscopically vary the intensity across the plane of exposure while keeping the other interference conditions, such as the angles between the light propagation vectors and the polarization, unchanged. One such variation of intensity would be a smooth gradient in intensity of one of the two interfering light waves. This results in interference fringes with uniform spacing but different intensities. The difference in intensity of the fringes leads to differences in exposure of the photoresist used. Because the fringe spacing is not changed, the pitch is uniform. The interference pattern would have even better contrast if both light waves had the same gradient in intensities.

When a positive photoresist is used, the areas corresponding to fringes with stronger intensities leave wider cavities in the photoresist after exposure and developing. The areas corresponding to fringes with weaker intensities leave narrower cavities in the photoresist. When the substrate is etched, these differing widths translate into features in the substrate that have differing widths. The features have the same pitch, however, because the fringe spacing is not altered. This leads to a constant pitch, but a varying line:space ratio. This procedure provides a continuously decreasing channel width that may be accurately controlled over very long distances. Such gradient separation matrices exhibit the favorable traits of gradient gels (high resolution in separation), without the difficulty and irreproducibility associated with their preparation.

Similarly, this technique, when used with a negative photoresist, leaves wider features in the areas corresponding to fringes with weaker intensity and narrower features in the areas corresponding to fringes with stronger intensity.

An alternative approach may produce features with a gradient in width and pitch. This may be easily achieved with IL by using a cylindrical lens in one of the beams, while keeping the other beam as a plane wave. In this case the plane of exposure becomes a chord for a number of circular wavefronts. Because the wavefronts have different radii of curvature (spacing of an optical wavelength), the spacing between the interference fringes, as well as the width of the interference fringes, vary along the length of the plane containing the interference fringes on the surface of the photoresist coating the substrate. Similarly, curved surfaces (sections of Newton's rings) may be formed by interfering a plane wave and a spherical wave or two spherical waves of differing radii of curvature.

Other types of separation systems may involve discontinuous gradients. One such system may have differing aperture sizes that may be produced by separate exposures with different intensities, at different pitches through shadow masks, or by using multiple exposure techniques to eliminate rows and/or columns of pillars in certain areas of a previously exposed uniform nano-structured surface.

Variations in size may also be produced chemically. For example, increasing the oxidation of silicon in certain areas of a chip may result in a swelling of the features, reducing the width of some channels while conserving the pitch of the features. Similarly, macroscopic areas may be selectively functionalized with monolayers, reducing the width of channels in that area.

One may also electrochemically produce silicon carbide on a silicon substrate. Silicon carbide is suitable for sublimation growth, allowing one to control the width of the modified channels in a certain area. Of course, silicon carbide is only one example of surface modifications that may be performed.

One may also selectively heat a substrate, bringing it close to its annealing temperature. At this time the substrate may be placed under a highly controlled stress. The subsequent strain alters the size of channels. A gradient in temperature across the substrate results in a gradient of strain, and therefore a gradient in channel widths. This technique would only be suitable for substrates without a crystalline structure (such as glass or amorphous silicon, for example).

The very high aspect ratios of FIGS. 5A and 5B were achieved using highly anisotropic wet chemical etching of crystalline Si in KOH, which exhibits a >400:1 etch-rate selectivity for etching the <100> plane relative to the <111> plane of Si. Thus, the vertical sidewalls are nearly perfect <111> Si facets. These structures may be further modified by oxidation. This provides insulation between the Si and the surrounding material (allowing electrophoretic fluidic manipulation) and varies the surface interactions between the nanostructure and the surrounding materials for fluidic applications. Very high aspect ratio, crystal-structure-independent etching processes have been developed to address the need for 3D structures in MEMs technology. These involve pulsed gas processes in which an isotropic etch process may be alternated with a surface passivation step to reduce the sidewall etch rate and only etch feature bottoms exposed by ion bombardment. To date, these processes have largely been investigated on micrometer scales. As part of the present invention, these processes are extended to the nanostructured regime. This greatly broadens the available classes of materials for which deep, high aspect ratio structures suitable for nanofluidic applications may be fabricated.

Nanostructures that exhibit a gradient in their capacity to transport biomolecular species (through size exclusion or otherwise) may be created by the IL processes discussed herein. Such gradients make separation matrices feasible for highly efficient separation of molecular species. Molecular species may be driven in the direction of the gradient, and thus separated based on their tendency to traverse the gradient, by a variety of driving forces, including, but not limited to, electrophoresis, externally-applied pressure, capillarity, diffusion, and osmosis.

IL represents a convenient method for generating nanostructured separation matrices that contain physical gradients that allow selective transport of chemical species and, thus, may be used to achieve a separation of different chemicals. When compared to other nanolithographic methods of pattern generation (e.g., electron beam lithography, scanning probe lithography), IL is more convenient, efficient and inexpensive because it may be used to generate the entire pattern in one, parallel step and is not a serial "writing" technique. Other parallel techniques (e.g., imprint lithography) rely on a primary patterning technique to generate a master that may then be used to produce replicas of nanostructured features in a parallel fashion. While IL is a preferred method to generate nanostructured gradients for molecular separation, a variety of methods could be employed to generate the nanostructured matrix gradient "artificial gels" of the present invention. Gradients in the chemistry of the separation matrix may be prepared by a variety of methods as well, including those based on IL.

The use of IL allows such nanostructured separation matrices to be produced easily and very inexpensively. Nanostructures in which channels are on the order of the excluded size of dissolved biomolecules allow an enhanced flexibility in separation. Higher resolution may be obtained in combination with any of the following mechanisms namely, size exclusion, electrophoretic mobility, isoelectric point, asymmetric diffusion, entropic trapping, hydrophobic interaction and affinity interaction (molecular recognition), as well as others. The gradient matrices produced allow efficient separation and identification of biomolecules such as native proteins and protein complexes in addition to denatured proteins and nucleic acids.

Nanolithography-generated systems have advantages over conventional systems in terms of (1) the virtually perfect uniformity of pore size and pore size distribution from device to device, and (2) the flexibility to precisely define the required distribution (gradient) of pore sizes and pore chemistries. This high degree of reproducibility and versatility in nanofabrication will result in the ability to construct separation devices that exhibit unprecedented degrees of flexibility (resolution, dynamic range) and reproducibility in their separation characteristics.

The separation gradient may be formed by a variety of means including, for example, nanolithography (e.g., IL, electron beam, local probe, nanoimprint) and pattern transfer (etching, deposition, lift-off) means.

Figure 6:
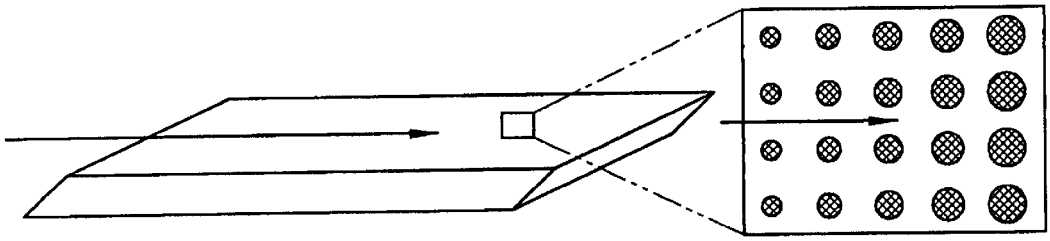
FIG. 6 illustrates in schematic form a nanostructured gradient (chirped) separation matrix.

FIG. 6 shows a schematic of a nanostructured gradient (chirped) separation matrix. The separation gradient may be formed by a variety of means including nanolithography (e.g., IL, electron beam, local probe, nanoimprint) and pattern transfer (etching, deposition, lift-oft) means. FIG. 6 illustrates a graded array of nanostructures. The aperture size between the nanostructures approaches molecular dimensions. The arrows signify the direction of movement of molecular species comprising the mixture to be separated and the direction of separation. The height of the nanostructures is preferably sufficiently larger (e.g., 100nm-1 μm) than the diameter to allow for higher throughput of the separated species.

Multiple-exposure IL moiré patterns provide for cyclic gradients that may be used for simultaneous manufacture of multiple structures. Gradients may also be fabricated across uniform patterns by non-uniform deposition or etching using properly designed deposition and/or etching tools and techniques such as oblique incidence of etch/deposition atomic/molecular species (shadowing). Analogous techniques may be used in generation of gradients in surface modification chemistry incorporated into the array.

Figure 7A:
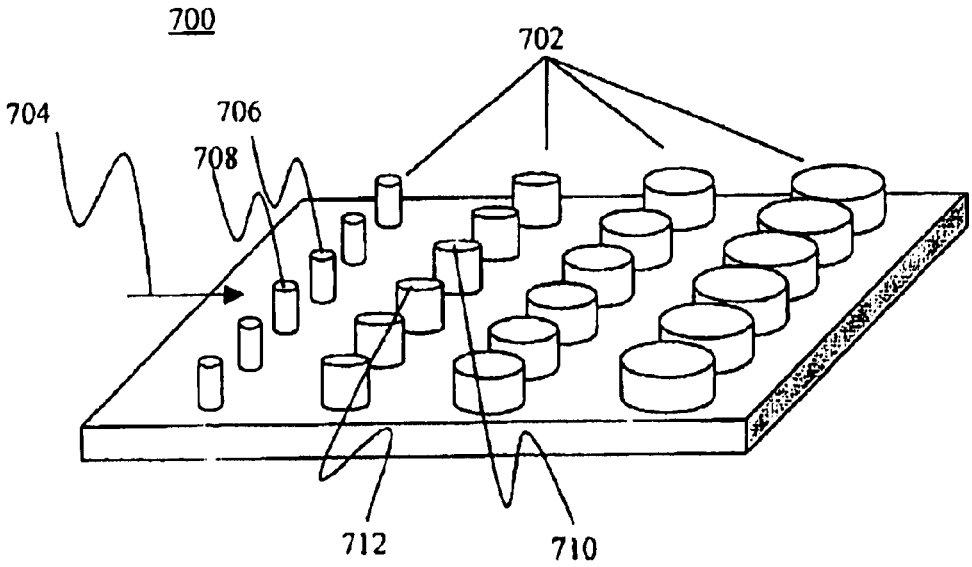
FIGS. 7A and 7B show perspective and top schematic views, respectively, of a nanostructured matrix according to the present invention.
Figure 7B:
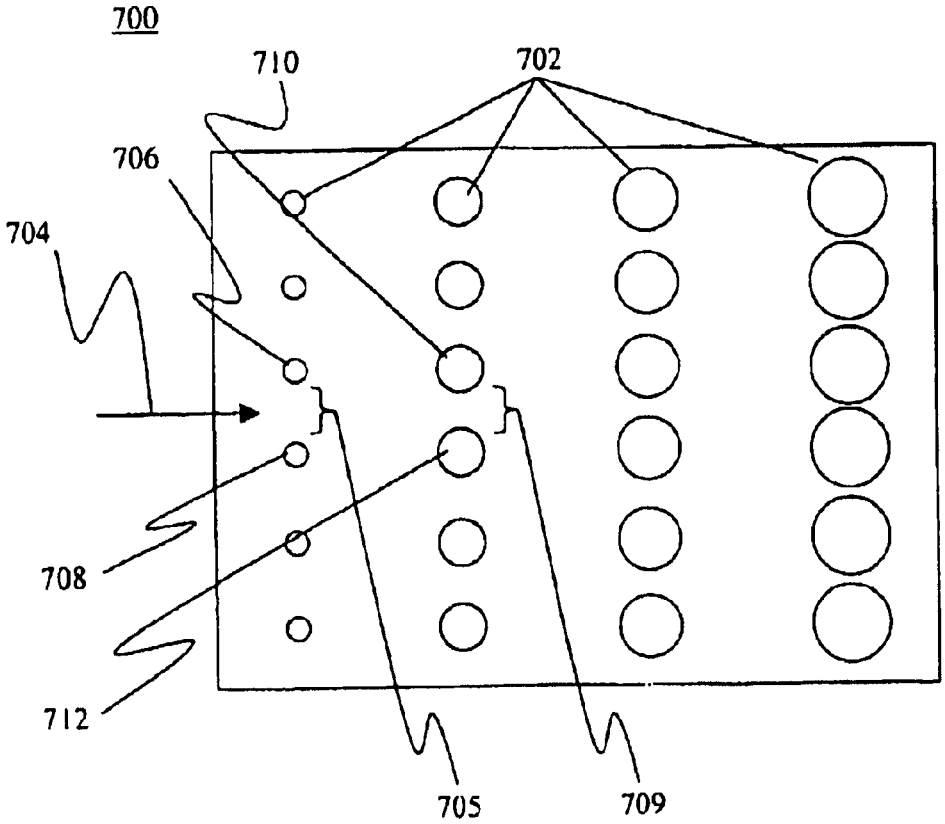

FIGS. 7A and 7B show a perspective view and a top view, respectively, of a nanostructured matrix according to the present invention. Matrix 700 has a plurality of protrusions 702. A sample containing some concentration of molecules moves in the direction of arrow 704. The diameter of channel 705 between protrusion 706 and protrusion 708 is larger than the diameter of channel 709 between protrusions 710 and 712. This change provides a gradient such that larger molecules are inhibited from moving the entire length of matrix 700 once the molecules encounter channels between two protrusions that are smaller than the diameter of the molecule. FIGS. 7A and 7B may be extended to formation of channels to delineate the pathway for molecule movement.

Figures 8A, 8B, 8C:
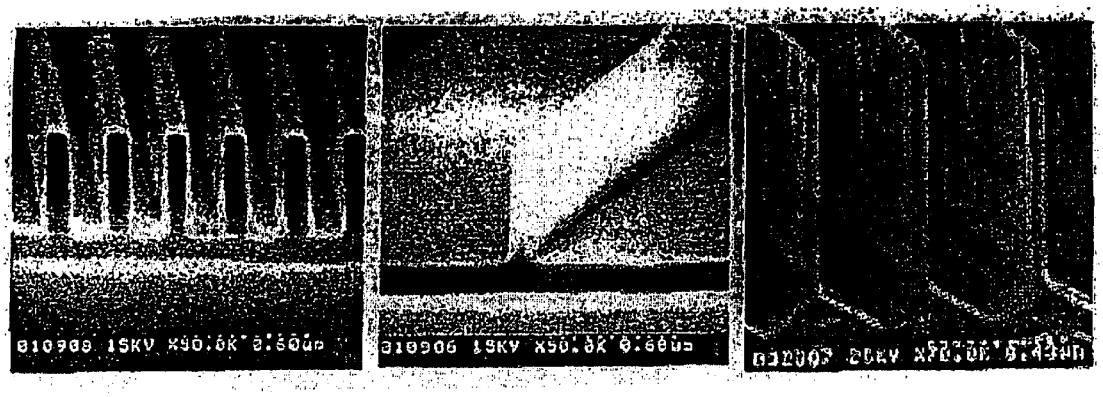
FIGS. 8A, 8B and 8C show high aspect ratio nanostructures fabricated by interferometric lithography and pattern transfer with FIG. 8A showing dense 150 nm photoresist lines, FIG. 8B showing an isolated 50 nm photoresist line, and FIG. 8C showing 50 nm wide walls etched in Si.

As an example of channel formation according to the present invention, IL and anisotropic wet etching of Si allow the creation of open, parallel nanostructured channels (e.g., uncapped in the direction perpendicular to the surface) with lateral features on the order of biomolecular length scales (~1-10 nm) but with overall dimensions reaching the microscopic (~100 μm) or even macroscopic (~1 cm or greater) scales. Depending upon the dimensions, molecular transport mechanisms may include diffusion, electrophoresis or bulk-flow. The relatively large vertical scale is sufficient to allow high throughput of molecules and external pumping using either electrokinetic or electro-osmotic forces. Examples of high aspect ratio IL nanostructured samples are shown in FIGS. 8A, 8B and 8C. Such architectures are applicable to channel and post arrays that are of interest for the separation of proteins and large DNA molecules.

Arrays of nanostructures (either of uniform size or with a gradient of sizes) may be surface-modified with chemical species that enhance the separation characteristics of the matrix. These chemical species may be distributed uniformly over the nanostructured separation matrix or may be distributed in a gradient (continuous or discrete) in the direction of separation over the matrix. These chemical species may include small organic molecules, polymers, receptors or other biomolecules.

IL may be used to expose patterns on photoresist on silicon or other materials (which may later be etched). Silicon and some other materials may have an oxide surface that is easily modified with silanization reagents. Synthetic strategies for modification are also available for other materials (besides oxides), including native silicon and noble metals (e.g., gold). Monomolecular layers may be created from a wide range of commercially-or synthetically-available chemical species that may enhance separation characteristics based on the type and degree of interaction of chemical species being separated with the walls of the surface-modified nanostructured separation matrix. Examples of types of surface modifications (either as gradients or uniform) include the use of hydrophilic oligomeric and polymeric species (e.g., poly-ethylene glycol (PEG)) to minimize interactions of chemical species, especially proteins, with nanostructured surfaces; use of hydrophobic molecular or oligomeric species to elicit hydrophobic interaction of chemical species (especially proteins) with nanostructured surfaces; use of mixtures of hydrophobic and hydrophilic species (polar, apolar, H-bonding, ionic) to tune interaction of different chemical species with surfaces; use of ionic molecular species and mixtures of ionic species to tune interaction of different chemical species with surfaces; use of biomolecular or organic receptors to elicit molecular recognition of small molecules, polymers, proteins, DNA, RNA, or oligonucleotides with the surface; use of oligonucleotide probes to tune interactions of DNA, RNA or nucleic-acid binding proteins with the surface; use of cyclodextrins, macrocyclic antibiotics, crown ethers and other chiral selectors to tune enantiomeric interactions of chemical species with the surface; and use of stimuli-responsive (smart) molecules or polymers to allow external control of interaction of chemical species with the nanostructured surface.

Other types of separation systems of the present invention may be thought of as having discontinuous gradients. These separation systems contain areas with different aperture sizes, and may be made either by separate exposures at different intensity, at different pitches through shadow masks, or by using multiple exposure techniques to eliminate rows and/or columns of pillars. Such systems are especially useful in that they will allow recovery of separated compounds (purification).

Microfabricated Integrated Multi-Dimensional, Multi-Technique Separation Systems The present invention allows a variety of different separation strategies (electrophoresis, iso-electric focusing, affinity chromatography, hydrophobic interaction chromatography, enantiomeric resolution) to be used on a single monolithic device, thus allowing for ease of use and compactness of instrumentation.

The closest existing commonly used multi-technique separation is two-dimensional gel electrophoresis (2DGE). In traditional 2DGE, proteins are first separated according to isoelectric point, followed by resolution by mass-to-charge ratio using standard polyacrylamide electrophoresis. This process requires that two separate electrophoretic procedures be performed, each requiring manipulation of the sample. A nanostructured matrix of the present invention allows for sequential analysis on a single chip, thus reducing sample loss and diffusion. The wide range of chemical modifications and array architecture allowed by IL devices will also permit separation of proteins by means in addition to size and isoelectric point, either by appropriate chemical patterning and valving of the device, or by addition of a third separation and/or dilution dimension.

Fabrication of separation matrix systems from materials (e.g., Si and quartz) commonly used in the fabrication of integrated circuits is advantageous. They have unique etching and surface modification characteristics that are well established, and may be easily implemented in existing microfabrication facilities for the development of complex separation and detection systems. Other materials with advantageous characteristics may also be used.

The nanostructured matrix of the present invention may be used for two-dimensional gel electrophoresis, and a number of other separation techniques may be combined with size exclusion and/or isoelectric focusing. In addition, the matrix has the capability of expansion beyond two dimensions.

Combining two or more standard types of analysis on a single platform may enhance the analytical potential of a nanostructured matrix of the present invention. Among the possible combinations of separation technologies applicable to this platform are those analogous to PAGE, isoelectric focusing, hydrophobic interaction chromatography, affinity chromatography, enantiomeric resolution and capillary electrophoresis. The matrix lends itself well to carrying out equivalent molecular weight separations, with either electrical currents or flow as the driving force.

The present invention may be useful in proteomics by enabling combinations of different types of analysis, e.g., size exclusion in one dimension with chemical differentiation in the second. A third dimension, oriented perpendicular to the two dimensional array, may then be used for further separation, or for recovery and further characterization of isolated spots.

The present invention may also find use in protein separations for forensic and medical diagnostic tools and in the separation of bioengineered proteins. Forensic analysis and diagnostics, for example, depend heavily upon differentiation between carbohydrate moieties on blood proteins and bacterial cells. Discovery of clinically useful drugs often depends on identifying interactions with specific cellular receptors, which are usually glycoproteins. Capillary electrophoresis has been extremely useful in separations of acid carbohydrates, with derivatization of the column. The present invention allows for the separation of two properties, for example glycoprotein size and carbohydrate content on a single platform, thus eliminating the need for cumbersome recovery between steps and increasing the yield of useful analyte.

Recently, techniques utilizing antibody-based affinity separations have transitioned from clinical laboratories to those for environmental monitoring. The present invention allows sequential analysis of at least two different properties, thus increasing sensitivity of analysis, with particular interest for environmental monitoring.

The present invention allows for separation of a variety of sizes of nucleic acid species, and thus, may be used for separations that are currently done by standard and pulsed field gel electrophoresis, as well as nucleic acid sequencing. In addition, modification of the device by nucleic acid binding molecules (e.g., proteins, drugs) allows for isolation of relevant target sequences from previously uncharacterized genomes, or for isolation of a biocomplex formed with a nucleic acid. Because separation may be multidimensional, these devices may be attached in series with a reaction chamber (for example, a PCR thermocycler) and the resultant product directly fed into the separation platform for purification and analysis in a single device.

IL may be used to create nanostructures on a variety of substrates. IL, in combination with other standard lithographic and microfabrication methodologies, may be used to create a variety of nanostructures that may be modified in many ways to produce tools for separation of relevant biomolecules. These have advantages over contemporary molecular separation systems because they exhibit superior performance (resolution, sensitivity, dynamic range, applicability, reproducibility), may be parallel-produced at relatively low cost, and are extremely flexible in terms of chemical modifications. They have defined features that may be reproducibly made, enable flexible and complex separation, and may be used with existing bioseparation and detection strategies.

Supported and Suspended Lipid Bilayers on Nanotextured Surfaces

An additional aspect of the present invention is the use of defined lithographic nanostructures to suspend or support lipid bilayers and hybrid lipid bilayers as a separation platform for membrane-associated biomolecules. This invention expands upon previous methods for (1) incorporating lipid bilayers and nanostructured surfaces for separation techniques, and (2) creating lipid bilayers in which regions of the lipid bilayers are freely suspended or supported between two aqueous reservoirs. Specifically, the present invention utilizes suspended or supported lipid bilayer architecture in the separation of transmembrane molecules.

FIG. 9 shows lipid bilayer 902 suspended on nanostructure 904. The dimensions of nanotroughs 906 are such that lipid bilayer 902 may be suspended on nanostructure 904 over the nanotrough, allowing for domains of biomolecules 908 exterior to the membrane to segregate into these troughs for separation. These structures are made by spontaneous assembly of lipid bilayers from lipid micelles on a hydrophilic surface. Transmembrane proteins and other biomolecules may be incorporated either during the formation of the micelles or formation of the membrane through fusion of micelles incorporating them or membrane ghosts. Certain membrane proteins are also capable of self-directed insertion into the membrane and these may be incorporated by direct insertion into the membrane.

FIGS. 10, 11 and 12 show various bilayers that may be associated with a particular nanostructure according to embodiments of the present invention. FIG. 10 shows a generic bilayer 1002 suspended on nanostructure 1004 over nanotroughs 1006. FIG. 11 shows a suspended lipid/self-assembled monolayer hybrid bilayer 1102 on nanostructure 1104 having nanotroughs 1106. This bilayer type of structure forms spontaneously when a monolayer containing hydrocarbon-like chains are present on the nanostructures. In this configuration, fluidity of the lower leaflets in the supported region is lost, as that leaflet is fixed. Transmembrane proteins and other membrane biomolecules are expected to move preferentially in those areas with greatest total membrane fluidity, i.e. in the troughs. It is also anticipated by the present invention that given formation conditions, e.g. size and curvature of the forming micelles in relation to the nanoarchitecture, that one may also achieve coverage of the bilayers over the entire surface, or over selected surfaces of the nanosupport. An example is represented in FIG. 12, which shows bilayer 1202 supported in nanotroughs 1206 in nanostructure 1204. This sort of structure may be achieved through selective modification of the tops of the nanostructures such that they would not support bilayer formation (e.g., hydrophobic modification) and through use of micelles that are smaller than the diameter of the nanotrough.

Of particular interest are nanofabricated arrays of structures that exhibit a gradient in their capacity to transport molecules. The reason being that such gradients allow for separation matrices that eliminate the requirement for detergent solubilization, and thus denaturation, of transmembrane biomolecules prior to separation, which is the current state of the art. Such gradient structures allow molecular species to be driven in the direction of the gradient, thereby separating the molecules based on their tendency to traverse the gradient. Molecular species may be driven across the gradient by forces such as electrophoresis, externally-applied pressure, capillarity, diffusion, and osmosis. Depending on the desired means of separation, several modifications of the nanostructured support that will enhance separation within the supported or suspended bilayer are envisioned. These include, but are not limited to chemical modifications, such as changes in hydrophobicity, charge, or dipole moment which will allow interactions with protein domains exterior to the bilayer, modification with ligands or other biomolecules that have the potential for interacting with a target class of membrane proteins, and other modifications that end users will deem necessary to base separations on membrane protein function.

Two relevant methods for fabricating suspended lipid bilayers have been reported: (1) suspending small unilamellar vesicles that are made and applied directly to an unmodified Si surface, and (2) generating large unilamellar vesicles with direct pipetting of these structures onto a surface. See, Groves, J. T., Wulfing, c., and Boxer, S. G., Electrical manipulation of glycan phosphatidyl inositol tethered proteins in planar supported bilayers, Biophysical Journal, 71: 2716-2723 (1996), and Menger, F. M., and Angelova, M. I., Accounts of Chemical Research, 31: 789-797 (1999), the entire contents and disclosures of which are hereby incorporated by reference. Preliminary studies included forming suspended lipid bilayers to examine their applicability in the present invention.

Since the electrophoretic mobility of transmembrane molecules across suspended lipid bilayers depends on (1) the molecule's mass to charge ratio, and (2) the size of the extramembrane domains relative to the corrugated apertures in the nanostructured support, it is necessary to fabricate a device that allows for preferential movement of molecules. An embodiment of the present invention suspends lipid bilayer membranes over a series of small gaps, approximately 100 nm in size, and utilizes the entire supported membrane as a separation and analysis platform. The small sizes of the gaps between features allows the lipid bilayer membrane to be suspended over the gaps, which allows for preferential movement of membrane phospholipids, transmembrane proteins, and other lipophilic biomolecules, and their complexes. More specifically, the relative fluidity of the lower leaflet of the lipid bilayer in the suspended regions, and resultant lack of steric hindrance of extramembrane protein domains, results in greater mobility of transmembrane molecules. Furthermore, by making the aperture size on the order of the molecular size of the transmembrane molecules, separations may be based on molecular filtering mechanisms in addition to electrophoretic mobility. Because the areas scanning the gaps may be supported on the underside by aqueous media, more room may also be available for intercellular domains. In addition, biophysical studies both of interactions between extra and intercellular domains of a single protein, and/or of interactions between intercellular domains of proteins within the same membrane are provided by the present invention. Thus, suspended lipid bilayer membranes offer several advantages over the current state of the art, particularly in regard to the separation and concentration of transmembrane proteins.

In a modification of the suspended lipid bilayer model, alkane-chain terminated self-assembled monolayers may be formed on the top surfaces of the nanostructured surfaces, either by silane modification of Si substrates or ω-substitued alkanethiols on, for example, gold. It is anticipated that these structures may provide even greater mobility of lipophilic biomolecules in supported and non-supported regions of the lipid bilayer membrane due to the immobility of the chemically fixed lower leaflet in the hybrid region.

Several nanotextured surfaces have also been explored. IL may produce a variety of features, including posts and grooves, in nearly infinite combinations of types and arrangements. Such features may be arranged in a regular array, thus mimicking standard gels, with the features either shaped or arranged in an asymmetric manner, or as semidiscontinuous, or chirped, arrays that vary in their size and/or separation distance along the direction of separation. Furthermore, a combination of grooves and/or posts may be arranged to achieve configurations that allow for two dimensional separations. The present invention may be used for separation of membranes from osmotically disrupted cells (cell ghosts). This is particularly significant because no previous isolation of membrane-associated biomolecules is necessary, thus preserving the biomolecules native conformations and complexes.

Although the present invention is primarily concerned with the structures described above, the nanostructured surfaces and lipid bilayer membranes may be combined in such a way to modify only the tops of the features, the lower surface of the nanostructured surface, the sides of the features, or any combination thereof. In addition, lipid bilayer membranes containing different molecules, or derived from different organelles within a cell, may be patterned on the nanostructured surface, thereby conferring a certain level of selectivity within the membrane itself, either due to innate properties of the molecules or the presence of interactive biomolecules within a region of the pattern. Thus, the present invention may be utilized in several manners to facilitate the study of biomolecules.

For instance, the nanostructured surfaces supporting lipid bilayer membranes may be utilized in biophysics to study membrane components. Because, within the suspended regions, neither leaflet of the membrane may be immobilized on the surface, total membrane fluidity may be increased, thus allowing for greater mobility of embedded biomolecules and creating an experimental milieu more closely replicating that found in the cell. Furthermore, interactions between cytoplasmic and extracellular domains may be more easily studied.

In addition, the present device shows promise as a biosensor device. Because the structure allows for proper orientation of the intercellular domains of transmembrane proteins, natural or engineered receptor proteins may take advantage of naturally occurring transduction mechanisms to facilitate signal transduction.

The present invention may further be useful in purification. The nanostructured lipid bilayer device may provide a unique platform on which to purify lipophilic membrane biomolecules. Because the components may be applied from membrane cell ghosts or in lipid micelles, the need for harsh and possibly denaturing detergent extraction may be unnecessary. In addition, complexes of associated proteins may be purified intact, thereby improving the study of pharmaceutical agents.

The present device may also be useful in the crystallization of membrane proteins to provide more pertinent information as to the structure and function of the proteins. The nanostructured lipid bilayer device may be manufactured to produce a gradient of features so that the protein in question aggregates at a single band in the device, thereby accumulating at the critical concentration.

Finally, the present invention may allow for greater flexibility in screening potential pharmaceutical agents. The nanostructured lipid bilayer device may facilitate observation of interactions between target transmembrane molecules and potential therapeutic agents within a defined membrane milieu, as well as allow for in vitro study of the resultant interactions between the drug-bound receptor and other components within the target complexes.

The present invention allows for unprecedented advances in the study of biomembranes and their associated molecules. The fact that membrane associated biomolecules may be applied to the present device, either via cell ghosts or vesicles, without first isolating them in aqueous media using detergent solubilization means that native configurations, associations and, thus, functionality may be preserved.

EXAMPLES

Example 1

Design and construction of microscale electrophoresis cells incorporated much of the characteristics of the present invention into a compact system. The cell preferably has the following characteristics: (1) electrochemical current and fluid flow is restricted to occur only through the separation matrix; (2) loading and stacking functions are included; (3) monitoring of mobility and biomolecular detection is possible (e.g., through fluorescence imaging); and (4) for certain applications, separated compounds are recoverable. Simple methods have been used for incorporating nanostructured silicon/silica chips into electrophoresis cells that satisfy criteria (1-3) above. For example, simple methods of rapid prototyping of elastomeric gasket materials have been used.

Example 2

Supported phospholipid bilayers (SPBs) of egg phosphatidyl choline (Egg PC) were formed by vesicle fusion on nanostructured silicon wafers containing troughs ~180 nm in width on a 360 nm pitch. An intercalating dye was introduced, and the membranes were imaged by scanning laser microscopy. The resultant fluorescence micrographs indicated that the SPBs formed uniformly over the surface and simple FRAP measurements indicated that the bilayers were fluid and that recovery of fluorescence was preferentially in the direction parallel to the nanotroughs.

Example 3

Transmembrane or membrane associated proteins may be incorporated into an SPB, from incorporation in the vesicle stage, insertion on the membrane or through incorporation of cell ghosts (i.e., intact membranes isolated from cells or organelles). The architecture and/or chemistry of the underlying nanotextured support would be then used to guide the movement of membrane proteins through the supported or suspended bilayer, either by size exclusion of the trough over which the membrane is supported, or by chemical interactions with modifications on the nanostructured support.

Although the present invention has been fully described in conjunction with the preferred embodiment thereof with reference to the accompanying drawings, it is to be understood that various changes and modifications may be apparent to those skilled in the art. Such changes and modifications are to be understood as included within the scope of the present invention as defined by the appended claims, unless they depart therefrom.

What is claimed is:

1. A nanostructured device comprising:

a substrate including *an upper face or surface and* at least one *elongate* nanotrough [therein] *extending downwardly into said substrate from said upper face or surface, said at least one elongate nanotrough having continuous or uninterrupted opposing walls along at least a substantial length thereof*; and

*a separation and analysis platform in the form of* a *singular continuous* lipid bilayer *in part disposed on said upper face or surface and in part* suspended over *or supported in* said at least one *elongate* nanotrough, *said lipid bilayer having sufficient fluidity to allow for mobility of biomolecules embedded within said lipid bilayer*.

2. The nanostructured device of claim 1, wherein said lipid bilayer comprises a simple bilayer.

3. The nanostructured device of claim 1, wherein said lipid bilayer comprises a hybrid bilayer.

4. The nanostructured device of claim 3, wherein said hybrid bilayer comprises a self-assembled monolayer hybrid bilayer.

5. The nanostructured device of claim 1, wherein said [nanostructured device further comprises an array of nanostructures arranged so that said array]*at least one nanotrough is filled with at least one fluid.*

6. The nanostructured device of claim 1, wherein said [nanostructured device further comprises an array of nanostructures arranged so that said array]*at least one elongate nanotrough* has a gradient property.

7. The nanostructured device of claim 1, wherein said nanostructured device further comprises at least one nanostructured channel.

8. The nanostructured device of claim 1, wherein said substrate comprises Si.

9. The nanostructured device of claim 1, wherein said substrate comprises a semiconductor chip.

10. The nanostructured device of claim 1, wherein said nanostructured device comprises a biochip.

11. A nanostructured device comprising:

a substrate including *a nanostructured matrix with an upper face or surface and* at least one *elongate* nanotrough [therein]*extending downwardly into said substrate from said upper face or surface*; and

*a separation and analysis platform in the form of* at least one *singular continuous* lipid bilayer *in part disposed on said upper face or surface and in part* supported in *or suspended over* [at least one of]said at least one *elongate* nanotrough[s so as to allow biomolecules to pass from said at least one lipid bilayer into said at least one respective nanotrough],

*said lipid bilayer having sufficient fluidity to allow for mobility of biomolecules embedded within said device so that said biomolecules are moveable to effectuate a separation of said biomolecules within said lipid bilayer.*

12. The nanostructured device of claim 11, wherein said lipid bilayer comprises a simple bilayer.

13. The nanostructured device of claim 11, wherein said lipid bilayer comprises a hybrid bilayer.

14. The nanostructured device of claim 13, wherein said hybrid bilayer comprises a self-assembled monolayer hybrid bilayer.

15. The nanostructured device of claim 11, wherein said nanostructured [device further comprises an array of nanostructures arranged so that said array]*matrix* has a gradient property.

16. The nanostructured device of claim 11, wherein said nanostructured device further comprises at least one nanostructured channel.

17. The nanostructured device of claim 11, wherein said substrate comprises Si.

18. The nanostructured device of claim 11, wherein said substrate comprises a semiconductor chip.

19. The nanostructured device of claim 11, wherein said nanostructured device comprises a biochip.

20. A separation method comprising the steps of:

(a) supporting or suspending *a separation and analysis platform in the form of* a lipid bilayer on a substrate; wherein said substrate comprises at least one [nanostructure]*elongate nanotrough, said nanotrough having continuous or uninterrupted opposing walls along at least a substantial length thereof*, and wherein said lipid bilayer [comprises at least one]*has sufficient fluidity to allow for mobility of* membrane associated biomolecules *embedded within said separation and analysis platform*; and (b) applying a driving force to said lipid bilayer to separate said [at least one]membrane associated biomolecules from [said lipid bilayer]*each other within said separation and analysis platform* and to drive said [at least one]membrane associated biomolecules within *and parallel to or in a plane of* said [lipid bilayer into]*separation and analysis platform by virtue of the fluidity of said lipid bilayer, and guided by* said at least one [nanostructure]*nanotrough*.

[21. The method of claim *20*, wherein said at least one nanostructure comprises at least one nanotrough.]

22. The method of claim *20*, wherein said at least one nanotrough is filled with at least one fluid.

23. The method of claim 20, wherein said at least one [nanostructure]*nanotrough* comprises at least one channel.

24. The method of claim 20, wherein said at least one [nanostructure]*nanotrough* further comprises at least [one]*two elongate* protrusions.

25. The method of claim 20, wherein said substrate comprises Si.

26. The method of claim 20, wherein said lipid bilayer comprises a simple bilayer.

27. The method of claim 20, wherein said lipid bilayer comprises a hybrid bilayer.

28. The method of claim 27, wherein said hybrid bilayer 25 comprises a self-assembled monolayer hybrid bilayer.

29. The method of claim 20, wherein said at least one[nanostructure]*nanotrough* [comprises an array of nanostructures arranged so that said array]has a gradient property.

30. The method of claim 20, wherein *at least one* of said [at least one]membrane associated biomolecule*s* comprises a transmembrane protein.

31. The method of claim 20, wherein [said at least one membrane associated biomolecule]*said lipid bilayer principally* comprises [a] *one or more* membrane phospholipid*s*.

32. The method of claim 20, wherein *at least one of* said [at least one]membrane associated biomolecule*s* comprises a lipophilic biomolecule.

33. The method of claim 20, wherein said driving force comprises an electrophoresis.

34. The method of claim 20, wherein said driving force comprises an externally applied pressure.

35. The method of claim 20, wherein said driving force comprises capillarity.

36. The method of claim 20, wherein said driving force comprises diffusion.

37. The method of claim 20, wherein said driving force comprises osmosis.

38. *A separation method comprising:*

*providing a nanostructured device comprising (i) a substrate including a nanostructured matrix with at least one elongate nanotrough therein, (ii) a separation and analysis platform in the form of a lipid bilayer suspended over or supported in said nanostructured matrix and said at least one elongate nanotrough, said lipid bilayer being derived from cell organelles, and (iii) a plurality of membrane-associated biomolecules occurring within said device and extending in said at least one elongate nanotrough, said lipid bilayer having sufficient fluidity to allow for mobility of biomolecules embedded within said device; and*

*applying a driving force to said lipid bilayer to drive said biomolecules within said device, by virtue of the fluidity of said lipid bilayer, and in said at least one elongate nanotrough, to separate said biomolecules from each other in said device under a screening action of said nanostructured matrix.*

39. *The method of claim 38, wherein said lipid bilayer comprises a simple bilayer.*

40. *The method of claim 38, wherein said lipid bilayer comprises a hybrid bilayer.*

41. *The method of claim 40, wherein said hybrid bilayer comprises a self-assembled monolayer hybrid bilayer.*

42. *The method of claim 38, wherein said at least one elongate nanotrough is filled with at least one fluid.*

43. *The method of claim 38, wherein said at least one elongate nantrough has a gradient property.*

44. *The method of claim 38, wherein said nanostructured device further comprises at least one nanostructured channel.*

45. *The method of claim 38, wherein said substrate comprises Si.*

46. *The method of claim 38, wherein said substrate comprises a semiconductor chip.*

47. *The method of claim 38, wherein said nanostructured device comprises a biochip.*

48. *The nanostructured device of claim 6, wherein said at least one elongate nanotrough has a varying width.*

49. *The method of claim 48 wherein said at least one elongate nanotrough has a continuously decreasing width.*

50. *The nanostructured device of claim 15, wherein said at least oen elongate nanotrough has a varying width.*

51. *The nanostructured device of claim 50, wherein said at least one elongate nanotrough has a continuously decreasing width.*

52. *The method of claim 29, wherein said at leat one elongate nanotrough has a varying width.*

53. *The method of claim 52, wherein said at least one elongate nanotrough has a continuously decreasing width.*

54. *The method of claim 43, wherein said at least one elongate nanotrough has a varying width.*

55. *The method of claim 54, wherein said at least one elongate nanotrough has a continuously decreasing width.*

* * * * *